United States Patent
Hause

(10) Patent No.: US 11,090,378 B2
(45) Date of Patent: Aug. 17, 2021

(54) PORCINE PARAINFLUENZA VIRUS COMPOSITIONS AND RELATED METHODS

(71) Applicant: Kansas Staten University Research Foundation, Manhattan, KS (US)

(72) Inventor: Ben Hause, Slayton, MN (US)

(73) Assignee: Kansas State University Research Foundation, Manhattan, KS (US)

( * ) Notice: Subject to any disclaimer, the term of this patent is extended or adjusted under 35 U.S.C. 154(b) by 314 days.

(21) Appl. No.: 16/067,909

(22) PCT Filed: Jan. 4, 2017

(86) PCT No.: PCT/US2017/012098
§ 371 (c)(1),
(2) Date: Jul. 3, 2018

(87) PCT Pub. No.: WO2017/120168
PCT Pub. Date: Jul. 13, 2017

(65) Prior Publication Data
US 2020/0261566 A1    Aug. 20, 2020

Related U.S. Application Data

(60) Provisional application No. 62/274,603, filed on Jan. 4, 2016.

(51) Int. Cl.
| | | |
|---|---|---|
| *A61K 31/10* | (2006.01) |
| *A61K 31/185* | (2006.01) |
| *A61K 31/285* | (2006.01) |
| *A61K 45/06* | (2006.01) |
| *C12N 15/113* | (2010.01) |
| *A61K 39/155* | (2006.01) |
| *A61P 37/04* | (2006.01) |
| *A61P 31/14* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/155* (2013.01); *A61K 39/39* (2013.01); *A61P 31/14* (2018.01); *A61P 37/04* (2018.01); *C12N 7/00* (2013.01); *A61K 2039/53* (2013.01); *A61K 2039/545* (2013.01); *A61K 2039/552* (2013.01); *C12N 2760/18034* (2013.01)

(58) Field of Classification Search
CPC ................ A61K 2300/00; A61K 31/10; C12Q 2521/301; C12Q 2525/301; C12Q 2537/101
See application file for complete search history.

(56) References Cited

U.S. PATENT DOCUMENTS 5,910,310 A * 6/1999 Heinen .................. A61K 39/12
424/211.1

OTHER PUBLICATIONS

Palinski et al., "Widespread detection and characterization of porcine parainfluenza virus 1 in pigs in the USA", J Gen Virol, 2015, 97:281-286.*

* cited by examiner

*Primary Examiner* — Barry A Chestnut
(74) *Attorney, Agent, or Firm* — Tracey S. Truitt; Armstrong Teasdale LLP

(57) ABSTRACT

The present disclosure provides the complete nucleotide sequence for porcine parainfluenza virus 1. Immunogenic compositions comprising portions of the nucleotide sequence and proteins expressed therefrom are also provided.

22 Claims, No Drawings
Specification includes a Sequence Listing.

PORCINE PARAINFLUENZA VIRUS COMPOSITIONS AND RELATED METHODS

This application contains a sequence listing in paper format and in computer readable format, the teachings and content of which are hereby incorporated by reference.

BACKGROUND

Paramyxoviruses are significant pathogens known to affect humans and a range of animals including livestock species such as cattle, pigs and poultry. These viruses are classified as members of the Paramyxoviridae family within the subfamily Paramyxovirinae. The subfamily Paramyxovirinae consists of seven genera: *Respirovirus, Rubulavirus, Avularvirus, Morbillivirus, Aquaparamyxovirus, Ferlavirus*, and *Henipavirus* (Lamb and Parks, 2007). The genus *Respirovirus* consists of five recognized species: bovine parainfluenza virus 3 (BPIV3), human parainfluenza virus 1 (HPIV1), human parainfluenza virus 3 (HPIV3), Sendai Virus (SeV), Simian virus 10 (SV10) and the proposed porcine parainfluenza virus 1 (PPIV1) (Lamb and Parks, 2007). Clinical symptoms are variable in terms of severity and presentation. While swine are the primary reservoir to porcine rubulavirus, cross species transmission of paramyxoviruses from their hosts to swine have been reported, including Nipah virus, Menangle virus, Newcastle disease virus and bovine parainfluenza virus 3 (Chua et al., 1999; Ellis, 2010; Janke et al., 2001; Philbey et al., 1998; Stephan et al., 1988). Importantly, many of these paramyxoviruses are zoonotic, some of which, namely Nipah virus and Hendra virus, have high fatality rates in humans (Chadha et al., 2006; Murray et al., 1995). Swine have been shown to serve as intermediate hosts for Nipah virus (McCormack, 2005).

In 2013, three complete genome sequences of a novel porcine parainfluenza virus, designated porcine parainfluenza virus 1 (PPIV1), were obtained from nasopharyngeal samples of slaughterhouse pigs in Hong Kong (Lau et al., 2013). Phylogenetic analysis of the nucleocapsid gene found PPIV1 to be most closely related to human parainfluenza virus-1 (HPIV1) and Sendai virus (SeV). While the nasal swabs were collected from deceased animals, nothing is known on the pathogenicity or ecology of PPIV1.

All viruses classified as Paramyxovirinae contain single stranded RNA genomes of approximately 15,000-16,000 bp in length which encodes for six proteins in the conserved order 3'-N-P-M-F-HN-L-5' where N, P, M, F, HN, and L represent the nucleocapsid, phosphoprotein, matrix protein, fusion protein, hemagglutinin-neuraminidase proteins and the polymerase protein, respectively (Lamb and Parks, 2007). Both F and HN proteins are involved in receptor binding, possess neutralizing epitopes and are the most genetically diverse viral proteins.

While PPIV1 has been identified in the U.S. by veterinary diagnostic laboratories in recent years, little is known on its epidemiology and role in clinical disease. There is only a single published report on the detection of the genetic signature of PPIV1 in the U.S. using microarray technology (Jaing et al., 2015). Here, next generation sequencing (NGS) performed on nasal swab samples from nursery pigs with respiratory disease from two separate facilities identified two complete genomes of PPIV1. Additionally, the pathogenesis of the virus was assessed in eleven naturally infected nursery pigs. Molecular epidemiological and serological analyses suggest the virus is common throughout the United States. What is needed is an immunogenic composition or vaccine against PPIV1.

SUMMARY OF THE INVENTION

The present disclosure provides for an immunogenic composition providing protection against infection by PPIV1. Further, a method for reducing the viral load of PPIV1 in an individual animal or group of animals is also provided as part of this disclosure. A method for reducing the symptoms of infections normally present with PPIV1 infection is also provided, where the method provides the step of administration of a PPIV1 immunogenic composition of the present invention.

The immunogenic composition of the present disclosure can either be a nucleic acid based immunogenic composition; a protein based immunogenic composition; a chimeric composition; or any combination thereof.

In one embodiment, a nucleic acid based immunogenic composition is provided. The nucleic acid is preferably selected from but not limited to, killed, inactivated, live, or modified live DNA or RNA. The nucleic acid is preferably selected from, but not limited to, SEQ ID No. 1 and SEQ ID No. 2. Preferably, the nucleic acid is a sequence that is at least 80%, at least 85%, at least 87%, at least 89%, at least 90%, at least 92%, or at least 95% homologous, to one of the following nucleotide sequences or a fragment thereof: SEQ ID No. 1 and SEQ ID No. 2. Some preferred fragments include the nucleic acid sequences coding for any one of the 6 genes as well as the open reading frames thereof.

In a further embodiment, a protein based immunogenic composition is provided. Preferably, the protein component is selected from, but not limited to, a recombinant protein, a harvested protein, a purified protein, and combinations thereof. In one preferred embodiment, a baculovirus recombinant viral vector containing a coding sequence selected from SEQ ID No. 1 and SEQ ID No.2 is provided. In one embodiment, the protein component is selected from, but not limited to, a protein encoded by one of the following sequences, a sequence that is at least 80%, at least 85%, at least 87%, at least 89%, at least 90%, at least 92%, or at least 95% homologous, to one of the following nucleotide sequences or a fragment thereof: SEQ ID No. 1 and SEQ ID No. 2. Some preferred fragments include the polypeptide sequences encoded by any one of the 6 genes as well as the open reading frames thereof.

A method for reducing the clinical symptoms associated with pathogens other than PPIV1 often found in an animal infected with PPIV1 is provided. The method preferably includes the steps of administration of the immunogenic composition of the present invention to an animal in need thereof. The clinical symptoms of pathogens to be reduced include, but not limited to, porcine astrovirus 4, porcine circovirus 2, porcine kobuvirus, porcine stool associated circular virus, and combinations thereof. Preferably the clinical symptoms associated with pathogens other than PPIV1 are reduced in frequency and/or severity by at least 10%, at least 20%, at least 30%, at least 40%, at least 50%, at least 60%, at least 70%, at least 80%, at least 90%, or reduced by 100%.

DETAILED DESCRIPTION

The immunogenic composition of the present disclosure can either be a nucleic acid based immunogenic composition; a protein based immunogenic composition; a chimeric composition; or a combination thereof.

The disclosure relates to the genome sequences and nucleotide sequences coding for polypeptides of, such as the structural and nonstructural polypeptides of a parainfluenza virus, as well as vectors including said sequences and cells or animals transformed by these vectors. The disclosure likewise relates to methods for detecting these nucleic acids or polypeptides and kits for diagnosing infection by porcine parainfluenza virus. The disclosure is also directed to a method for selecting compounds capable of modulating the viral infection. The disclosure further comprises pharmaceutical compositions, including vaccines, for the prevention and/or the treatment of viral infections by porcine parainfluenza virus 1 (PPIV1) as well as the use of a vector according to the disclosure for the prevention and/or the treatment of diseases by gene therapy.

The present disclosure relates to vaccines comprising a nucleotide sequence of the genome of porcine parainfluenza virus 1, SEQ ID No. 1, SEQ ID NO. 2, or a homologue or fragment thereof, and an acceptable pharmaceutical or veterinary vehicle. In one embodiment of the disclosure, the nucleotide sequence is selected from, or a homologue or fragment thereof. In another embodiment of the disclosure, the homologue has at least 80% sequence identity to SEQ ID No. 1 or SEQ ID No. 2. In yet another embodiment, the vaccines further comprise an adjuvant.

The present disclosure also relates to vaccines comprising a polypeptide encoded by a nucleotide sequence of the genome of PPIV1, or a homologue or fragment thereof, and an acceptable pharmaceutical or veterinary vehicle. In one embodiment, the homologue has at least 80% sequence identity to SEQ ID No. 1 (GenBank Accession No. KT749882) or SEQ ID No. 2 (GenBank Accession No. KT749893). Preferably, the nucleotide sequence is a sequence that is at least 80%, at least 85%, at least 87%, at least 89%, at least 90%, at least 92%, or at least 95% homologous, to one of the following nucleotide sequences or a fragment thereof: SEQ ID No. 1 or SEQ ID No. 2.

A further aspect of the disclosure relates to vaccines comprising a vector and an acceptable pharmaceutical or veterinary vehicle, the vector comprising a nucleotide sequence of the genome of porcine parainfluenza virus 1, or a homologue or fragment thereof. In one embodiment, the vaccine further comprises a gene coding for an expression product capable of inhibiting or retarding the establishment or development of a genetic or acquired disease.

The present disclosure also relates to vaccines comprising a cell and an acceptable pharmaceutical or veterinary vehicle, wherein the cell is transformed with a nucleotide sequence of the genome of porcine parainfluenza virus 1, or a homologue or fragment thereof.

Still further, the present disclosure relates to vaccines comprising a pharmaceutically acceptable vehicle and a single polypeptide, wherein the single polypeptide consists of SEQ ID No. 1 or SEQ ID No. 2.

Additionally, the present disclosure relates to methods of immunizing a mammal against porcine parainfluenza virus 1 comprising administering to a mammal an effective amount of the vaccines described above. These and other aspects of the disclosure will become apparent to the skilled artisan in view of the teachings contained herein.

The present disclosure relates to nucleotide sequences of the genome of porcine parainfluenza virus 1 selected from the sequences SEQ ID No. 1, SEQ ID No. 2 or one of their fragments.

The present disclosure likewise relates to nucleotide sequences, characterized in that they are selected from:
 a) a nucleotide sequence of a specific modified fragment of the sequence SEQ ID No. 1, SEQ ID No. 2 or one of their fragments;
 b) a nucleotide sequence homologous to a nucleotide sequence such as defined in a);
 c) a nucleotide sequence complementary to a nucleotide sequence such as defined in a) or b), and a nucleotide sequence of their corresponding RNA;
 d) a nucleotide sequence capable of hybridizing under stringent conditions with a sequence such as defined in a), b) or c);
 e) a nucleotide sequence comprising a sequence such as defined in a), b), c) or d); and
 f) a nucleotide sequence modified by a nucleotide sequence such as defined in a), b), c), d) or e).

Nucleotide, polynucleotide or nucleic acid sequence will be understood according to the present disclosure as meaning both a double-stranded or single-stranded DNA in the monomeric and dimeric (so-called in tandem) forms and the transcription products of said DNAs.

It must be understood that the present disclosure does not relate to the genomic nucleotide sequences taken in their natural environment, that is to say, in the natural state. It concerns sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors.

Nucleotide sequence fragment according to the disclosure will be understood as designating any nucleotide fragment of the porcine parainfluenza virus 1, of length of at least 8 nucleotides, preferably at least 12 nucleotides, and even more preferentially at least 20 consecutive nucleotides of the sequence from which it originates.

Specific modified fragment of a nucleotide sequence according to the disclosure will be understood as designating any nucleotide fragment of the porcine parainfluenza virus 1, having, after alignment and comparison with the corresponding fragments of known porcine parainfluenza viruses, at least one nucleotide or base of different nature.

Homologous nucleotide sequence in the sense of the present disclosure is understood as meaning a nucleotide sequence having at least a percentage identity with the bases of a nucleotide sequence according to the disclosure of at least 80%, where ranges and values, including but not limited to, from 80% to 85%, 85% to 96%, 80% to 95%, 90% to 99%, 88% to 98%, 80%, 81%, 82%, 83%, 84%, 85%, 86%, 87%, 88%, 89%, 90%, 91%, 92%, 93%, 94%, 95%, 95.5%, 96%, 96.5%, 97%, 97.5%, 98%, 98.5%, 99%, 99.5%, 99.9%, and higher are envisioned, where this percentage being purely statistical and it being possible to distribute the differences between the two nucleotide sequences at random and over the whole of their length.

Specific homologous nucleotide sequence in the sense of the present disclosure is understood as meaning a homologous nucleotide sequence having at least one nucleotide sequence of a specific modified fragment, such as defined above. Said "specific" homologous sequences can comprise, for example, the sequences corresponding to the genomic sequence or to the sequences of its fragments representative of variants of porcine parainfluenza virus 1. These specific homologous sequences can thus correspond to variations linked to mutations within strains of porcine parainfluenza virus 1, and especially correspond to truncations, substitutions, deletions and/or additions of at least one nucleotide. Said homologous sequences can likewise correspond to variations linked to the degeneracy of the genetic code.

The term "degree or percentage of sequence homology" refers to "degree or percentage of sequence identity between two sequences after optimal alignment" as defined in the present application.

Two amino-acids or nucleotidic sequences are said to be "identical" if the sequence of amino-acids or nucleotidic residues, in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Neddleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

"Percentage of sequence identity" (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well-defined and only one value for the sequence identity between two compared sequences which value corresponds to the value obtained for the best or optimal alignment.

In the BLAST N or BLAST P "BLAST 2 sequence", software which is available in the web site ncbi.nlm.nih.gov/gorf/b12.html, and habitually used by the inventors and in general by the skilled man for comparing and determining the identity between two sequences, gap cost which depends on the sequence length to be compared is directly selected by the software (i.e. 11.2 for substitution matrix BLOSUM-62 for length >85).

Mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

In the present description, porcine parainfluenza virus 1 will be understood as designating the parainfluenza viruses that replicate in respiratory epithelial cells of the upper respiratory tract and exhibits nasal shedding similar to established swine respiratory disease etiologic agents, defined below by their genomic sequence, as well as the parainfluenza viruses whose nucleic sequences are homologous to the sequences of porcine parainfluenza virus 1.

Complementary nucleotide sequence of a sequence of the disclosure is understood as meaning any DNA whose nucleotides are complementary to those of the sequence of the disclosure, and whose orientation is reversed (antiparallel sequence).

Hybridization under conditions of stringency with a nucleotide sequence according to the disclosure is understood as meaning a hybridization under conditions of temperature and ionic strength chosen in such a way that they allow the maintenance of the hybridization between two fragments of complementary DNA.

Among the nucleotide sequences according to the disclosure, those are likewise preferred which can be used as a primer or probe in methods allowing the homologous sequences according to the disclosure to be obtained, these methods, such as the polymerase chain reaction (PCR), nucleic acid cloning and sequencing, being well known to the person skilled in the art.

Among said nucleotide sequences according to the disclosure, those are again preferred which can be used as a primer or probe in methods allowing the presence of porcine parainfluenza virus 1 or one of its variants such as defined below to be diagnosed.

The nucleotide sequences according to the disclosure capable of modulating, of inhibiting or of inducing the expression of porcine parainfluenza virus 1 gene, and/or capable of modulating the replication cycle of porcine parainfluenza virus 1 in the host cell and/or organism are likewise preferred. Replication cycle will be understood as designating the invasion and the multiplication of porcine parainfluenza virus 1, and its propagation from host cell to host cell in the host organism.

Among said nucleotide sequences according to the disclosure, those corresponding to six proteins conserved, which are the nucleocapsid (N), phosphoprotein (P), matrix protein (M), fusion protein (F), hemmagglutinin-neuraminidase proteins (HN) and the polymerase protein (L). The nucleotide sequence fragments according to the disclosure can be obtained, for example, by specific amplification, such as PCR, or after digestion with appropriate restriction enzymes of nucleotide sequences according to the disclosure, these methods in particular being described in the work of Sambrook et al., 1989. Said representative fragments can likewise be obtained by chemical synthesis when their size is not very large and according to methods well known to persons skilled in the art.

Modified nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle.

Modified nucleotide sequence will likewise be understood as meaning any nucleotide sequence coding for a modified polypeptide such as defined below.

The present disclosure relates to nucleotide sequences of porcine parainfluenza virus 1 according to the disclosure, characterized in that they are selected from the sequences SEQ ID No. 1, SEQ ID No.2, or one of their fragments.

The disclosure likewise relates to nucleotide sequences characterized in that they comprise a nucleotide sequence selected from:

a) a nucleotide sequence SEQ ID No. 1, SEQ ID No. 2, or one of their fragments;
b) a nucleotide sequence of a specific modified fragment of a sequence such as defined in a);
c) a homologous nucleotide sequence having at least 80% identity with a sequence such as defined in a) or b);
d) a complementary nucleotide sequence or sequence of RNA corresponding to a sequence such as defined in a), b) or c); and
e) a nucleotide sequence modified by a sequence such as defined in a), b), c) or d).

As far as homology with the nucleotide sequences SEQ ID No. 1, SEQ ID No. 2, or one of their fragments is concerned, the homologous, especially specific, sequences having a percentage identity with one of the sequences SEQ ID No. 1, SEQ ID No. 2, or one of their fragments of at least 80%, preferably 90% or 95%, are preferred. Said specific homologous sequences can comprise, for example, the sequences corresponding to the proteins of porcine parainfluenza virus 1. In the same manner, these specific homologous sequences can correspond to variations linked to mutations within strains of porcine parainfluenza virus 1 and especially correspond to truncations, substitutions, deletions and/or additions of at least one nucleotide.

The disclosure also relates to the polypeptides, characterized in that they comprise a polypeptide selected from:

a) a specific modified fragment of at least 5 amino acids of a polypeptide of an amino acid sequence according to the disclosure;
b) a polypeptide homologous to a polypeptide such as defined in a);
c) a specific biologically active fragment of a polypeptide such as defined in a) or b); and
d) a polypeptide modified by a polypeptide such as defined in a), b) or c).

Among the polypeptides according to the disclosure, the polypeptides encoded by SEQ ID No. 1 and SEQ ID No. 2, a fragment thereof, or one of the six genes of porcine parainfluenza virus 1 are also preferred, these polypeptides being especially capable of specifically recognizing the antibodies produced during infection by the porcine parainfluenza virus 1. These polypeptides thus have epitopes specific for the porcine parainfluenza virus 1 and can thus be used in particular in the diagnostic field or as immunogenic agent to confer protection in pigs against infection by porcine parainfluenza virus 1.

In the present description, the terms polypeptide, peptide and protein are interchangeable.

It must be understood that the disclosure does not relate to the polypeptides in natural form, that is to say that they are not taken in their natural environment but that they can be isolated or obtained by purification from natural sources, or else obtained by genetic recombination, or alternatively by chemical synthesis and that they can thus contain unnatural amino acids, as will be described below.

Polypeptide fragment according to the disclosure is understood as designating a polypeptide containing at least 5 consecutive amino acids, preferably 10 consecutive amino acids or 15 consecutive amino acids.

In the present disclosure, specific polypeptide fragment is understood as designating the consecutive polypeptide fragment encoded by a specific modified fragment nucleotide sequence according to the disclosure.

Homologous polypeptide will be understood as designating the polypeptides having, with respect to the natural polypeptide, certain modifications such as, in particular, a deletion, addition or substitution of at least one amino acid, a truncation, a prolongation, a chimeric fusion, and/or a mutation. Among the homologous polypeptides, those are preferred whose amino acid sequence has at least 80%, homology with the sequences of amino acids of polypeptides according to the disclosure, where values and ranges, including but not limited to, from 80% to 85%, 85% to 96%, 80% or 95%, 80% to 99%, 90% to 97%, 80% to 85%, 85% to 96%, 80%, 81%, 82%, 83%, 84%, 85%, 86%, 87%, 88%, 89%, 90%, 91%, 92%, 93%, 94%, 95%, 95.5%, 96%, 96.5%, 97%, 97.5%, 98%, 98.5%, 99%, 99.5%, 99.9%, and higher are envisioned.

Specific homologous polypeptide will be understood as designating the homologous polypeptides such as defined above and having a specific modified fragment of polypeptide according to the disclosure.

In the case of a substitution, one or more consecutive or nonconsecutive amino acids are replaced by "equivalent" amino acids. The expression "equivalent" amino acid is directed here at designating any amino acid capable of being substituted by one of the amino acids of the base structure without, however, essentially modifying the biological activities of the corresponding peptides and such that they will be defined by the following.

These equivalent amino acids can be determined either by depending on their structural homology with the amino acids which they substitute, or on results of comparative tests of biological activity between the different polypeptides, which are capable of being carried out.

By way of example, the possibilities of substitutions capable of being carried out without resulting in an extensive modification of the biological activity of the corresponding modified polypeptides will be mentioned, the replacement, for example, of leucine by valine or isoleucine, of aspartic acid by glutamic acid, of glutamine by asparagine, of arginine by lysine etc., the reverse substitutions naturally being envisageable under the same conditions.

The specific homologous polypeptides likewise correspond to polypeptides encoded by the specific homologous nucleotide sequences such as defined above and thus comprise in the present definition the polypeptides which are mutated or correspond to variants which can exist in porcine parainfluenza virus 1, and which especially correspond to truncations, substitutions, deletions and/or additions of at least one amino acid residue.

Specific biologically active fragment of a polypeptide according to the disclosure will be understood in particular as designating a specific polypeptide fragment, such as defined above, having at least one of the characteristics of polypeptides according to the disclosure, especially in that it is:

capable of inducing an immunogenic reaction directed against a porcine parainfluenza virus 1; and/or capable of being recognized by a specific antibody of a polypeptide according to the disclosure; and/or capable of linking to a polypeptide or to a nucleotide sequence of porcine parainfluenza virus 1; and/or capable of exerting a physiological activity, even partial, such as, for example, a dissemination or structural (capsid) activity; and/or capable of modulating, of inducing or of inhibiting the expression of porcine parainfluenza virus 1 gene or one of its variants, and/or capable of modulating the replication cycle of porcine parainfluenza virus 1 in the cell and/or the host organism.

The polypeptide fragments according to the disclosure can correspond to isolated or purified fragments naturally present in a porcine parainfluenza virus 1, correspond to one of the six genes of PPV1, or correspond to fragments which can be obtained by cleavage of said polypeptide by a proteolytic enzyme, such as trypsin or chymotrypsin or collagenase, or by a chemical reagent, such as cyanogen bromide (CNBr) or alternatively by placing said polypeptide in a very acidic environment, for example at pH 2.5. Such polypeptide fragments can likewise just as easily be prepared by chemical synthesis, from hosts transformed by an expression vector according to the disclosure containing a nucleic acid allowing the expression of said fragments, placed under the control of appropriate regulation and/or expression elements.

"Modified polypeptide" of a polypeptide according to the disclosure is understood as designating a polypeptide obtained by genetic recombination or by chemical synthesis as will be described below, having at least one modification with respect to the normal sequence. These modifications will especially be able to bear on amino acids at the origin of a specificity, of pathogenicity and/or of virulence, or at the origin of the structural conformation, and of the capacity of membrane insertion of the polypeptide according to the disclosure. It will thus be possible to create polypeptides of equivalent, increased or decreased activity, and of equivalent, narrower, or wider specificity. Among the modified polypeptides, it is necessary to mention the polypeptides in which up to 5 amino acids can be modified, truncated at the N- or C-terminal end, or even deleted or added.

As is indicated, the modifications of the polypeptide may have as an objective: to render it capable of modulating, of inhibiting or of inducing the expression of porcine parainfluenza virus 1 gene and/or capable of modulating the replication cycle of porcine parainfluenza virus 1 in the cell and/or the host organism, of allowing its incorporation into vaccine compositions, or of modifying its bioavailability as a compound for therapeutic use.

The methods allowing said modulations on eukaryotic or prokaryotic cells to be demonstrated are well known to the person skilled in the art. It is likewise well understood that it will be possible to use the nucleotide sequences coding for said modified polypeptides for said modulations, for example through vectors according to the disclosure and described below, in order, for example, to prevent or to treat the pathologies linked to the infection.

The preceding modified polypeptides can be obtained by using combinatorial chemistry, in which it is possible to systematically vary parts of the polypeptide before testing them on models, cell cultures or microorganisms for example, to select the compounds which are most active or have the properties sought.

Chemical synthesis likewise has the advantage of being able to use: unnatural amino acids, or non-peptide bonds.

Thus, in order to improve the duration of life of the polypeptides according to the disclosure, it may be of interest to use unnatural amino acids, for example in D form, or else amino acid analogs, especially sulfur-containing forms, for example.

Finally; it will be possible to integrate the structure of the polypeptides according to the disclosure, its specific or modified homologous forms, into chemical structures of polypeptide type or others. Thus, it may be of interest to provide at the N- and C-terminal ends compounds not recognized by the proteases.

The nucleotide sequences coding for a polypeptide according to the disclosure are likewise part of the disclosure.

The disclosure likewise relates to nucleotide sequences utilizable as a primer or probe, characterized in that said sequences are selected from the nucleotide sequences according to the disclosure.

The cloning and the sequencing of the porcine parainfluenza virus 1, has allowed it to be identified, after comparative analysis with the nucleotide sequences of other porcine parainfluenza viruses, that, among the sequences of fragments of these nucleic acids, were those which are strictly specific to the porcine parainfluenza virus 1 and those which correspond to a consensus sequence of porcine parainfluenza viruses other than the porcine parainfluenza virus 1. There is likewise a great need for nucleotide sequences utilizable as a primer or probe specific to the whole of the other known and nonpathogenic porcine parainfluenza viruses.

It is well understood that the present disclosure likewise relates to specific polypeptides of known porcine parainfluenza viruses other than porcine parainfluenza virus 1, encoded by said consensus nucleotide sequences, capable of being obtained by purification from natural polypeptides, by genetic recombination or by chemical synthesis by procedures well known to the person skilled in the art and such as described in particular below. In the same manner, the labeled or unlabeled mono- or polyclonal antibodies directed against said specific polypeptides encoded by said consensus nucleotide sequences are also part of the disclosure.

It will be possible to use said consensus nucleotide sequences, said corresponding polypeptides as well as said antibodies directed against said polypeptides in procedures or sets for detection and/or identification such as described below, in place of or in addition to nucleotide sequences, polypeptides or antibodies according to the disclosure, specific to porcine parainfluenza virus 1.

The disclosure additionally relates to the use of a nucleotide sequence according to the disclosure as a primer or probe for the detection and/or the amplification of nucleic acid sequences. The nucleotide sequences according to the disclosure can thus be used to amplify nucleotide sequences, especially by the PCR technique (polymerase chain reaction) (Erlich, 1989; Innis et al., 1990; Rolfs et al., 1991; and White et al., 1997). These oligodeoxyribonucleotide or oligoribonucleotide primers advantageously have a length of at least 8 nucleotides, preferably of at least 12 nucleotides, and even more preferentially at least 20 nucleotides.

Other amplification techniques of the target nucleic acid can be advantageously employed as alternatives to PCR.

The nucleotide sequences of the disclosure, in particular the primers according to the disclosure, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the disclosure can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example an MRNA, it will be possible to use, prior to the employment of an amplification reaction with the aid of at least one primer according to the disclosure or to the employment of a detection procedure with the aid of at least one probe of the disclosure, an enzyme of reverse transcriptase type in order to obtain a cDNA from the RNA contained in the biological sample. The cDNA obtained will thus serve as a target for the primer(s) or the probe(s) employed in the amplification or detection procedure according to the disclosure.

The detection probe will be chosen in such a manner that it hybridizes with the target sequence or the amplicon generated from the target sequence. By way of sequence, such a probe will advantageously have a sequence of at least 12 nucleotides, in particular of at least 20 nucleotides, and preferably of at least 100 nucleotides.

The disclosure also comprises the nucleotide sequences utilizable as a probe or primer according to the disclosure, characterized in that they are labeled with a radioactive compound or with a nonradioactive compound.

The unlabeled nucleotide sequences can be used directly as probes or primers, although the sequences are generally labeled with a radioactive element ($^{32}P$, $^{35}S$, $^{3}H$, $^{125}I$) or with a nonradioactive molecule (biotin, acetylaminofluorene, digoxigenin, 5-bromodeoxyuridine, fluorescein) to obtain probes which are utilizable for numerous applications.

Examples of nonradioactive labeling of nucleotide sequences are described, for example, in French Patent No. 78.10975 or by Urdea et al. or by Sanchez-Pescador et al. in 1988. In the latter case, it will also be possible to use one of the labeling methods described in patents FR-2 422 956 and FR-2 518 755.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe).

The disclosure likewise comprises the nucleotide sequences according to the disclosure, characterized in that they are immobilized on a support, covalently or noncovalently.

According to another advantageous mode of employing nucleotide sequences according to the disclosure, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

Another subject of the present disclosure is a vector for the cloning and/or expression of a sequence, characterized in that it contains a nucleotide sequence according to the disclosure.

The vectors according to the disclosure, characterized in that they contain the elements allowing the expression and/or the secretion of said nucleotide sequences in a determined host cell, are likewise part of the disclosure.

The vector must then contain a promoter, signals of initiation and termination of translation, as well as appropriate regions of regulation of transcription. It must be able to be maintained stably in the host cell and can optionally have particular signals specifying the secretion of the translated protein. These different elements are chosen as a function of the host cell used. To this end, the nucleotide sequences according to the disclosure can be inserted into autonomous replication vectors within the chosen host, or integrated vectors of the chosen host.

Such vectors will be prepared according to the methods currently used by the person skilled in the art, and it will be possible to introduce the clones resulting therefrom into an appropriate host by standard methods, such as, for example, lipofection, electroporation and thermal shock. The vectors according to the disclosure are, for example, vectors of plasmid or viral origin.

These vectors are useful for transforming host cells in order to clone or to express the nucleotide sequences of the disclosure.

The disclosure likewise comprises the host cells transformed by a vector according to the disclosure. These cells can be obtained by the introduction into host cells of a nucleotide sequence inserted into a vector such as defined above, then the culturing of said cells under conditions allowing the replication and/or expression of the transfected nucleotide sequence.

The host cell can be selected from prokaryotic or eukaryotic systems, such as, for example, bacterial cells (Olins and Lee, 1993), but likewise yeast cells (Buckholz, 1993), as well as animal cells, in particular the cultures of mammalian cells (Edwards and Aruffo, 1993), and especially Chinese hamster ovary (CHO) cells, but likewise the cells of insects in which it is possible to use procedures employing baculoviruses, for example (Luckow, 1993). A preferred host cell for the expression of the proteins of the disclosure is constituted by sf9 insect cells.

The disclosure likewise relates to animals comprising one of said transformed cells according to the disclosure. The obtainment of transgenic animals according to the disclosure overexpressing one or more of the genes of porcine parainfluenza virus 1 or part of the genes will be preferably carried out in rats, mice or rabbits according to methods well known to the person skilled in the art, such as by viral or nonviral transfections. It will be possible to obtain the transgenic animals overexpressing one or more of said genes by transfection of multiple copies of said genes under the control of a strong promoter of ubiquitous nature, or selective for one type of tissue. It will likewise be possible to obtain the transgenic animals by homologous recombination in embryonic cell strains, transfer of these cell strains to embryos, selection of the affected chimeras at the level of the reproductive lines, and growth of said chimeras.

The transformed cells as well as the transgenic animals according to the disclosure are utilizable in procedures for preparation of recombinant polypeptides. It is today possible to produce recombinant polypeptides in relatively large quantity by genetic engineering using the cells transformed by expression vectors according to the disclosure or using transgenic animals according to the disclosure.

The procedures for preparation of a polypeptide of the disclosure in recombinant form, characterized in that they employ a vector and/or a cell transformed by a vector according to the disclosure and/or a transgenic animal comprising one of said transformed cells according to the disclosure, are themselves comprised in the present disclosure.

Among said procedures for preparation of a polypeptide of the disclosure in recombinant form, the preparation procedures employing a vector, and/or a cell transformed by said vector and/or a transgenic animal comprising one of said transformed cells, containing a nucleotide sequence according to the disclosure coding for a polypeptide of porcine parainfluenza virus 1, are preferred.

The recombinant polypeptides obtained as indicated above can just as well be present in glycosylated form as in nonglycosylated form and can or cannot have the natural tertiary structure.

A preferred variant consists in producing a recombinant polypeptide used to a "carrier" protein (chimeric protein). The advantage of this system is that it allows a stabilization of and a decrease in the proteolysis of the recombinant product, an increase in the solubility in the course of renaturation in vitro and/or a simplification of the purification when the fusion partner has an affinity for a specific ligand.

More particularly, the disclosure relates to a procedure for preparation of a polypeptide of the disclosure comprising the following steps:
  a) culture of transformed cells under conditions allowing the expression of a recombinant polypeptide of nucleotide sequence according to the disclosure;
  b) if need be, recovery of said recombinant polypeptide.

When the procedure for preparation of a polypeptide of the disclosure employs a transgenic animal according to the disclosure, the recombinant polypeptide is then extracted from said animal. The present disclosure also relates to a polypeptide which is capable of being obtained by a procedure of the disclosure such as described previously.

The disclosure also comprises a procedure for preparation of a synthetic polypeptide, characterized in that it uses a sequence of amino acids of polypeptides according to the disclosure. The disclosure likewise relates to a synthetic polypeptide obtained by a procedure according to the disclosure. The polypeptides according to the disclosure can likewise be prepared by techniques which are conventional in the field of the synthesis of peptides. This synthesis can be carried out in homogeneous solution or in solid phase.

For example, recourse can be made to the technique of synthesis in homogeneous solution described by Houben-Weyl in 1974. This method of synthesis consists of successively condensing, two by two, the successive amino acids in the order required, or in condensing amino acids and fragments formed previously and already containing several amino acids in the appropriate order, or alternatively several fragments previously prepared in this way, it being understood that it will be necessary to protect beforehand all the reactive functions carried by these amino acids or fragments, with the exception of amine functions of one and carboxyls of the other or vice-versa, which must normally be involved in the formation of peptide bonds, especially after activation of the carboxyl function, according to the methods well known in the synthesis of peptides.

According to another preferred technique of the disclosure, recourse will be made to the technique described by Merrifield. To make a peptide chain according to the Merrifield procedure, recourse is made to a very porous polymeric resin, on which is immobilized the first C-terminal amino acid of the chain. This amino acid is immobilized on a resin through its carboxyl group and its amine function is protected. The amino acids which are going to form the peptide chain are thus immobilized, one after the other, on the amino group, which is deprotected beforehand each time, of the portion of the peptide chain already formed, and which is attached to the resin. When the whole of the desired peptide chain has been formed, the protective groups of the different amino acids forming the peptide chain are eliminated and the peptide is detached from the resin with the aid of an acid.

The disclosure additionally relates to hybrid polypeptides having at least one polypeptide according to the disclosure, and a sequence of a polypeptide capable of inducing an immune response in man or animals. Advantageously, the antigenic determinant is such that it is capable of inducing a humoral and/or cellular response. It will be possible for such a determinant to comprise a polypeptide according to the disclosure in glycosylated form used with a view to obtaining immunogenic compositions capable of inducing the synthesis of antibodies directed against multiple epitopes. Said polypeptides or their glycosylated fragments are likewise part of the disclosure.

These hybrid molecules can be formed, in part, of a polypeptide carrier molecule or of fragments thereof according to the disclosure, associated with a possibly immunogenic part, in particular an epitope of the diphtheria toxin, the tetanus toxin, a surface antigen of the hepatitis B virus (patent FR 79 21811), the VP1 antigen of the poliomyelitis virus or any other viral or bacterial toxin or antigen.

The procedures for synthesis of hybrid molecules encompass the methods used in genetic engineering for constructing hybrid nucleotide sequences coding for the polypeptide sequences sought. It will be possible, for example, to refer advantageously to the technique for obtainment of genes coding for fusion proteins described by Minton in 1984. Said hybrid nucleotide sequences coding for a hybrid polypeptide as well as the hybrid polypeptides according to the disclosure characterized in that they are recombinant polypeptides obtained by the expression of said hybrid nucleotide sequences are likewise part of the disclosure.

The disclosure likewise comprises the vectors characterized in that they contain one of said hybrid nucleotide sequences. The host cells transformed by said vectors, the transgenic animals comprising one of said transformed cells as well as the procedures for preparation of recombinant polypeptides using said vectors, said transformed cells and/or said transgenic animals are, of course, likewise part of the disclosure.

The polypeptides according to the disclosure, the antibodies according to the disclosure described below and the nucleotide sequences according to the disclosure can advantageously be employed in procedures for the detection and/or identification of porcine parainfluenza virus 1, or of porcine parainfluenza virus other than a porcine parainfluenza virus 1, in a biological sample (biological tissue or fluid) capable of containing them. These procedures, according to the specificity of the polypeptides, the antibodies and the nucleotide sequences according to the disclosure which will be used, will in particular be able to detect and/or to identify a porcine parainfluenza virus 1 or a porcine parainfluenza virus other than a porcine parainfluenza virus 1.

The polypeptides according to the disclosure can advantageously be employed in a procedure for the detection and/or the identification of porcine parainfluenza virus 1 in a biological sample (biological tissue or fluid) capable of containing them, characterized in that it comprises the following steps:
  a) contacting of this biological sample with a polypeptide or one of its fragments according to the disclosure (under conditions allowing an immunological reaction between said polypeptide and the antibodies possibly present in the biological sample);
  b) demonstration of the antigen-antibody complexes possibly formed.

Preferably, the biological sample is formed by a fluid, for example a pig serum, whole blood or biopsies. Any conventional procedure can be employed for carrying out such a detection of the antigen-antibody complexes possibly formed. By way of example, a preferred method brings into play immunoenzymatic processes according to the ELISA technique, by immunofluorescence, or radioimmunological processes (RIA) or their equivalent.

Thus, the disclosure likewise relates to the polypeptides according to the disclosure, labeled with the aid of an adequate label such as of the enzymatic, fluorescent or radioactive type.

Such methods comprise, for example, the following steps: deposition of determined quantities of a polypeptide composition according to the disclosure in the wells of a microtiter plate, introduction into said wells of increasing dilutions of serum, or of a biological sample other than that defined previously, having to be analyzed, incubation of the microplate, introduction into the wells of the microtiter plate of labeled antibodies directed against pig immunoglobulins, the labeling of these antibodies having been carried out with the aid of an enzyme selected from those which are capable of hydrolyzing a substrate by modifying the absorption of the radiation of the latter, at least at a determined wavelength, for example at 550 nm, detection, by comparison with a control test, of the quantity of hydrolyzed substrate.

The disclosure likewise relates to a kit or set for the detection and/or identification of porcine parainfluenza virus 1, characterized in that it comprises the following elements: a polypeptide according to the disclosure, if need be, the reagents for the formation of the medium favorable to the immunological or specific reaction, if need be, the reagents allowing the detection of the antigen-antibody complexes produced by the immunological reaction between the polypeptide(s) of the disclosure and the antibodies possibly present in the biological sample, these reagents likewise being able to carry a label, or to be recognized in their turn by a labeled reagent, more particularly in the case where the polypeptide according to the disclosure is not labeled, if need be, a biological reference sample (negative control) devoid of antibodies recognized by a polypeptide according to the disclosure, if need be, a biological reference sample (positive control) containing a predetermined quantity of antibodies recognized by a polypeptide according to the disclosure.

The polypeptides according to the disclosure allow monoclonal or polyclonal antibodies to be prepared which are characterized in that they specifically recognize the polypeptides according to the disclosure. It will advantageously be possible to prepare the monoclonal antibodies from hybridomas according to the technique described by Kohler and Milstein in 1975. It will be possible to prepare the polyclonal antibodies, for example, by immunization of an animal, in particular a mouse, with a polypeptide or a DNA, according to the disclosure, associated with an adjuvant of the immune response, and then purification of the specific antibodies contained in the serum of the immunized animals on an affinity column on which the polypeptide which has served as an antigen has previously been immobilized. The polyclonal antibodies according to the disclosure can also be prepared by purification, on an affinity column on which a polypeptide according to the disclosure has previously been immobilized, of the antibodies contained in the serum of pigs infected by a porcine parainfluenza virus 1.

The disclosure likewise relates to mono- or polyclonal antibodies or their fragments, or chimeric antibodies, characterized in that they are capable of specifically recognizing a polypeptide according to the disclosure.

It will likewise be possible for the antibodies of the disclosure to be labeled in the same manner as described previously for the nucleic probes of the disclosure, such as a labeling of enzymatic, fluorescent or radioactive type.

The disclosure is additionally directed at a procedure for the detection and/or identification of porcine parainfluenza virus 1, in a biological sample, characterized in that it comprises the following steps:
  a) contacting of the biological sample (biological tissue or fluid) with a mono- or polyclonal antibody according to the disclosure (under conditions allowing an immunological reaction between said antibodies and the polypeptides of porcine parainfluenza virus 1, possibly present in the biological sample);
  b) demonstration of the antigen-antibody complex possibly formed.

Likewise within the scope of the disclosure is a kit or set for the detection and/or the identification of porcine parainfluenza virus 1, characterized in that it comprises the following components:
  a polyclonal or monoclonal antibody according to the disclosure, if need be labeled; if need be, a reagent for the formation of the medium favorable to the carrying out of the immunological reaction;
  if need be, a reagent allowing the detection of the antigen-antibody complexes produced by the immunological reaction, this reagent likewise being able to carry a label, or being capable of being recognized in its turn by a labeled reagent, more particularly in the case where said monoclonal or polyclonal antibody is not labeled;
  if need be, reagents for carrying out the lysis of cells of the sample tested.

The present disclosure likewise relates to a procedure for the detection and/or the identification of porcine parainfluenza virus 1 in a biological sample, characterized in that it employs a nucleotide sequence according to the disclosure.

More particularly, the disclosure relates to a procedure for the detection and/or the identification of porcine parainfluenza virus 1, in a biological sample, characterized in that it contains the following steps:
  a) if need be, isolation of the DNA from the biological sample to be analyzed;
  b) specific amplification of the DNA of the sample with the aid of at least one primer, or a pair of primers, according to the disclosure;
  c) demonstration of the amplification products.

These can be detected, for example, by the technique of molecular hybridization utilizing a nucleic probe according to the disclosure. This probe will advantageously be labeled with a nonradioactive (cold probe) or radioactive element.

For the purposes of the present disclosure, "DNA of the biological sample" or "DNA contained in the biological sample" will be understood as meaning either the DNA present in the biological sample considered, or possibly the cDNA obtained after the action of an enzyme of reverse transcriptase type on the RNA present in said biological sample.

Another aim of the present disclosure consists in a procedure according to the disclosure, characterized in that it comprises the following steps:
  a) contacting of a nucleotide probe according to the disclosure with a biological sample, the DNA contained in the biological sample having, if need be, previously been made accessible to hybridization under conditions allowing the hybridization of the probe with the DNA of the sample;
  b) demonstration of the hybrid formed between the nucleotide probe and the DNA of the biological sample.

The present disclosure also relates to a procedure according to the disclosure, characterized in that it comprises the following steps:
  a) contacting of a nucleotide probe immobilized on a support according to the disclosure with a biological sample, the DNA of the sample having, if need be, previously been made accessible to hybridization, under conditions allowing the hybridization of the probe with the DNA of the sample;
  b) contacting of the hybrid formed between the nucleotide probe immobilized on a support and the DNA contained in the biological sample, if need be after elimination of the DNA of the biological sample which has not hybridized with the probe, with a nucleotide probe labeled according to the disclosure;
  c) demonstration of the novel hybrid formed in step b).

According to an advantageous embodiment of the procedure for detection and/or identification defined previously, this is characterized in that, prior to step a), the DNA of the biological sample is first amplified with the aid of at least one primer according to the disclosure.

The disclosure is additionally directed at a kit or set for the detection and/or the identification of porcine parainfluenza virus 1, characterized in that it comprises the following elements:
  a) a nucleotide probe according to the disclosure;
  b) if need be, the reagents necessary for the carrying out of a hybridization reaction;
  c) if need be, at least one primer according to the disclosure as well as the reagents necessary for an amplification reaction of the DNA.

The disclosure likewise relates to a kit or set for the detection and/or the identification of porcine parainfluenza virus 1, of porcine parainfluenza Virus other than a porcine parainfluenza virus 1 or of porcine parainfluenza Virus other than the porcine parainfluenza virus 1, characterized in that it comprises the following components:
  a) a nucleotide probe, called a capture probe, according to the disclosure;
  b) an oligonucleotide probe, called a revealing probe, according to the disclosure,
  c) if need be, at least one primer according to the disclosure, as well as the reagents necessary for an amplification reaction of the DNA.

The disclosure also relates to a kit or set for the detection and/or identification of porcine parainfluenza virus 1, characterized in that it comprises the following elements:
  a) at least one primer according to the disclosure;
  b) if need be, the reagents necessary for carrying out a DNA amplification reaction;
  c) if need be, a component allowing the sequence of the amplified fragment to be verified, more particularly an oligonucleotide probe according to the disclosure.

The disclosure additionally relates to the use of a nucleotide sequence according to the disclosure, of a polypeptide according to the disclosure, of an antibody according to the disclosure, of a cell according to the disclosure, and/or of an animal transformed according to the disclosure, for the selection of an organic or inorganic compound capable of modulating, inducing or inhibiting the expression of genes, and/or of modifying the cellular replication of porcine parainfluenza virus 1 or capable of inducing or of inhibiting the pathologies linked to an infection by a porcine parainfluenza virus 1.

The disclosure likewise comprises a method of selection of compounds capable of binding to a polypeptide or one of its fragments according to the disclosure, capable of binding to a nucleotide sequence according to the disclosure, or capable of recognizing an antibody according to the disclosure, and/or capable of modulating, inducing or inhibiting the expression of genes, and/or of modifying the cellular replication of porcine parainfluenza virus 1 or capable of inducing or inhibiting the pathologies linked to an infection by a porcine parainfluenza virus 1, characterized in that it comprises the following steps:

a) contacting of said compound with said polypeptide, said nucleotide sequence, or with a cell transformed according to the disclosure and/or administration of said compound to an animal transformed according to the disclosure;

b) determination of the capacity of said compound to bind to said polypeptide or said nucleotide sequence, or to modulate, induce or inhibit the expression of genes, or to modulate the growth or the replication of porcine parainfluenza virus 1, or to induce or inhibit in said transformed animal the pathologies linked to an infection by porcine parainfluenza virus 1 (designated activity of said compound).

Inhibiting the pathologies linked to an infection by porcine parainfluenza virus 1 will include reducing the severity of or the incidence of the pathologies, or clinical signs, or clinical symptoms, linked to, associated with, or caused by porcine parainfluenza virus 1.

The compounds capable of being selected can be organic compounds such as polypeptides or carbohydrates or any other organic or inorganic compounds already known, or novel organic compounds elaborated by molecular modelling techniques and obtained by chemical or biochemical synthesis, these techniques being known to the person skilled in the art.

It will be possible to use said selected compounds to modulate the cellular replication of porcine parainfluenza virus 1 and thus to control infection by this virus, the methods allowing said modulations to be determined being well known to the person skilled in the art.

This modulation can be carried out, for example, by an agent capable of binding to a protein and thus of inhibiting or of potentiating its biological activity, or capable of binding to an envelope protein of the external surface of said virus and of blocking the penetration of said virus into the host cell or of favoring the action of the immune system of the infected organism directed against said virus. This modulation can likewise be carried out by an agent capable of binding to a nucleotide sequence of a DNA of said virus and of blocking, for example, the expression of a polypeptide whose biological or structural activity is necessary for the replication or for the proliferation of said virus host cells to host cells in the host animal.

The disclosure relates to the compounds capable of being selected by a selection method according to the disclosure. The disclosure likewise relates to a pharmaceutical composition comprising a compound selected from the following compounds:

a) a nucleotide sequence according to the disclosure;
    b) a polypeptide according to the disclosure;
    c) a vector, a viral particle or a cell transformed according to the disclosure;
    d) an antibody according to the disclosure;
    e) a compound capable of being selected by a selection method according to the disclosure; possibly in combination with a pharmaceutically acceptable vehicle and, if need be, with one or more adjuvants of the appropriate immunity.

The disclosure also relates to an immunogenic and/or vaccine composition, characterized in that it comprises a compound selected from the following compounds:

a) a nucleotide sequence according to the disclosure;
    b) a polypeptide according to the disclosure;
    c) a vector or a viral particle according to the disclosure; and
    d) a cell according to the disclosure.

In one embodiment, the vaccine composition according to the disclosure is characterized in that it comprises a mixture of at least two of said compounds a), b), c) and d) above and in that one of the two said compounds is related to the porcine parainfluenza virus 1.

In another embodiment of the disclosure, the vaccine composition is characterized in that it comprises at least one compound a), b), c), or d) above which is related to porcine parainfluenza virus 1. In still another embodiment, the vaccine composition is characterized in that it comprises at least one compound a), b), c), or d) above which is related to porcine parainfluenza virus 1.

A compound related to the porcine parainfluenza virus 1 is understood here as respectively designating a compound obtained from the genomic sequence of the porcine parainfluenza virus 1 and/or any one or more of the six genes of porcine parainfluenza virus 1.

The disclosure is additionally aimed at an immunogenic and/or vaccine composition, characterized in that it comprises at least one of the following compounds:

a nucleotide sequence SEQ ID No. 1, SEQ ID No. 2 or one of their fragments or homologues;

a polypeptide of sequence encoded by SEQ ID No. 1, SEQ ID No. 2 or one of their fragments, or a modification thereof;

a vector or a viral particle comprising a nucleotide sequence SEQ ID No. 1, SEQ ID No. 2, or one of their fragments or homologues;

a transformed cell capable of expressing a polypeptide encoded by the nucleotide sequence of SEQ ID No. 1, SEQ ID No. 2, or one of their fragments including one of the six genes of porcine parainfluenza 1, or a modification thereof; or a mixture of at least two of said compounds.

The disclosure also comprises an immunogenic and/or vaccine composition according to the disclosure, characterized in that it comprises said mixture of at least two of said compounds as a combination product for simultaneous, separate or protracted use for the prevention or the treatment of infection by a porcine parainfluenza virus 1.

In a preferred embodiment, the vaccine composition according to the disclosure comprises the mixture of the following compounds:

a pcDNA3 plasmid containing a nucleic acid of sequence SEQ ID No. 1;

a pcDNA3 plasmid containing a nucleic acid of sequence SEQ ID No. 2;

a pcDNA3 plasmid containing a nucleic acid coding for the GM-CSF protein;

a recombinant baculovirus containing a nucleic acid of sequence SEQ ID No. 1;

a recombinant baculovirus containing a nucleic acid of sequence SEQ ID No. 2; and if need be, an adjuvant of the appropriate immunity.

The disclosure is likewise directed at a pharmaceutical composition according to the disclosure, for the prevention or the treatment of an infection by a porcine parainfluenza virus 1. The disclosure likewise concerns the use of a composition according to the disclosure, for the preparation of a medicament intended for the prevention or the treatment of infection by a porcine parainfluenza virus 1.

Under another aspect, the disclosure relates to a vector, a viral particle or a cell according to the disclosure, for the treatment and/or the prevention of a disease, especially one related to, associated with, or caused by porcine parainfluenza virus 1, by gene therapy.

Finally, the disclosure comprises the use of a vector, of a viral particle or of a cell according to the disclosure for the preparation of a medicament intended for the treatment and/or the prevention of a disease, especially one related to, associated with, or caused by porcine parainfluenza virus 1, by gene therapy.

The polypeptides of the disclosure entering into the immunogenic or vaccine compositions according to the disclosure can be selected by techniques known to the person skilled in the art such as, for example, depending on the capacity of said polypeptides to stimulate the T cells, which is translated, for example, by their proliferation or the secretion of interleukins, and which leads to the production of antibodies directed against said polypeptides.

In pigs, as in mice, in which a weight dose of the vaccine composition comparable to the dose used in man is administered, the antibody reaction is tested by taking of the serum followed by a study of the formation of a complex between the antibodies present in the serum and the antigen of the vaccine composition, according to the usual techniques.

The pharmaceutical compositions according to the disclosure will contain an effective quantity of the compounds of the disclosure, that is to say in sufficient quantity of said compound(s) allowing the desired effect to be obtained, such as, for example, the modulation of the cellular replication of porcine parainfluenza virus 1. The person skilled in the art will know how to determine this quantity, as a function, for example, of the age and of the weight of the individual to be treated, of the state of advancement of the pathology, of the possible secondary effects and by means of a test of evaluation of the effects obtained on a population range, these tests being known in these fields of application.

According to the disclosure, said vaccine combinations will preferably be combined with a pharmaceutically acceptable vehicle and, if need be, with one or more adjuvants of the appropriate immunity.

Today, various types of vaccines are available for protecting animals or man against infectious diseases: attenuated living microorganisms (*M. bovis*—BCG for tuberculosis), inactivated microorganisms (influenza virus), a cellular extracts (*Bordetella* pertussis for whooping cough), recombined proteins (surface antigen of the hepatitis B virus), polysaccharides (pneumococcal). Vaccines prepared from synthetic peptides or genetically modified microorganisms expressing heterologous antigens are in the course of experimentation. More recently still, recombined plasmid DNAs carrying genes coding for protective antigens have been proposed as an alternative vaccine strategy. In some forms, this type of vaccination is carried out with a particular plasmid originating from a plasmid of *E. coli* which does not replicate in vivo and which codes uniquely for the vaccinating protein. Animals have been immunized by simply injecting the naked plasmid DNA into the muscle. This technique leads to the expression of the vaccine protein in situ and to an immune response of cellular type (CTL) and of humoral type (antibody). This double induction of the immune response is one of the principal advantages of the vaccination technique with naked DNA.

The vaccine compositions comprising nucleotide sequences or vectors into which are inserted said sequences are especially described in the international application No. WO 90/11092 and likewise in the international application No. WO 95/11307.

The constitutive nucleotide sequence of the vaccine composition according to the disclosure can be injected into the host after having been coupled to compounds which favor the penetration of this polynucleotide into the interior of the cell or its transport to the cell nucleus. The resultant conjugates can be encapsulated in polymeric microparticles, as described in the international application No. WO 94/27238 (Medisorb Technologies International).

According to another embodiment of the vaccine composition according to the disclosure, the nucleotide sequence, preferably a DNA, is complexed with DEAE-dextran (Pagano et al., 1967) or with nuclear proteins (Kaneda et al., 1989), with lipids (Felgner et al., 1987) or encapsulated in liposomes (Fraley et al., 1980) or else introduced in the form of a gel facilitating its transfection into the cells (Midoux et al., 1993, Pastore et al., 1994). The polynucleotide or the vector according to the disclosure can also be in suspension in a buffer solution or be combined with liposomes.

Advantageously, such a vaccine will be prepared according to the technique described by Tacson et al. or Huygen et al. in 1996 or alternatively according to the technique described by Davis et al. in the international application No. WO 95/11307.

Such a vaccine can likewise be prepared in the form of a composition containing a vector according to the disclosure, placed under the control of regulation elements allowing its expression in man or animal. It will be possible, for example, to use, by way of in vivo expression vector of the polypeptide antigen of interest, the plasmid pcDNA3 or the plasmid pcDNA1/neo, both marketed by Invitrogen (R&D Systems, Abingdon, United Kingdom). It is also possible to use the plasmid V1Jns.tPA, described by Shiver et al. in 1995. Such a vaccine will advantageously comprise, apart from the recombinant vector, a saline solution, for example a sodium chloride solution.

Pharmaceutically acceptable vehicle is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound.

As far as the vaccine formulations are concerned, these can comprise adjuvants of the appropriate immunity which are known to the person skilled in the art, such as, for example, aluminum hydroxide, a representative of the family of muramyl peptides such as one of the peptide derivatives of N-acetyl muramyl, a bacterial lysate, one of the many types of Carbopol, or alternatively Freund's incomplete adjuvant.

These compounds can be administered by the systemic route, in particular by the intravenous route, by the intramuscular, intradermal or subcutaneous route, or by the oral route. In a more preferred manner, the vaccine composition comprising polypeptides according to the disclosure will be administered by the intramuscular route, through the food, or by nebulization several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective against piglet weight loss disease.

For example, in the case of a vaccine according to the present disclosure comprising a polypeptide encoded by a nucleotide sequence of the genome of PPIV1, or a homolgue or fragment thereof, the polypeptide will be administered one time or several times, spread out over time, directly or by means of a transformed cell capable of expressing the polypeptide, in an amount of about 0.1 to 1000 µg per kilogram weight of the animal, where values and ranges such as, but not limited to, 0.5 to 800 µg per kilogram weight of the animal, 1 to 1000 µg per kilogram weight of the animal, 1 to 500 µg per kilogram weight of the animal, 1 to 300 µg per kilogram weight of the animal, 1 to 200 µg per kilogram weight of the animal, 1 to 150 µg per kilogram weight of the animal 1 to 125 µg per kilogram weight of the animal, 1 to 100 µg per kilogram weight of the animal, 5 µg per kilogram weight of the animal, 10 µg per kilogram weight of the animal, 15 µg per kilogram weight of the animal, 20 µg per kilogram weight of the animal, 25 µg per kilogram weight of the animal, 30 µg per kilogram weight of the animal, 35 µg per kilogram weight of the animal, 40 µg per kilogram weight of the animal, 45 µg per kilogram weight of the animal, 50 µg per kilogram weight of the animal, 55 µg per kilogram weight of the animal, 60 µg per kilogram weight of the animal, 65 µg per kilogram weight of the animal, 70 µg per kilogram weight of the animal, 75 µg per kilogram weight of the animal, 80 µg per kilogram weight of the animal, 85 µg per kilogram weight of the animal, 90 µg per kilogram weight of the animal, 95 µg per kilogram weight of the animal, 100 µg per kilogram weight of the animal, 125 µg per kilogram weight of the animal, 150 µg per kilogram weight of the animal, 200 µg per kilogram weight of the animal, 250 µg per kilogram weight of the animal, 300 µg per kilogram weight of the animal, 400 µg per kilogram weight of the animal, 500 µg per kilogram weight of the animal, 600 µg per kilogram weight of the animal, 700 µg per kilogram weight of the animal, 800 µg per kilogram weight of the animal, 900 µg per kilogram weight of the animal, and 1000 µg per kilogram weight of the animal are envisioned. In other preferred forms, the above amounts are also provided without reference to the weight of the animal.

The present disclosure likewise relates to the use of nucleotide sequences of porcine parainfluenza virus 1 according to the disclosure for the construction of autoreplicative retroviral vectors and the therapeutic applications of these, especially in the field of human gene therapy in vivo.

The feasibility of gene therapy applied to man no longer needs to be demonstrated and this relates to numerous therapeutic applications like genetic diseases, infectious diseases and cancers. Numerous documents of the prior art describe the means of employing gene therapy, especially through viral vectors. Generally speaking, the vectors are obtained by deletion of at least some of the viral genes which are replaced by the genes of therapeutic interest. Such vectors can be propagated in a complementation line which supplies in trans the deleted viral functions in order to generate a defective viral vector particle for replication but capable of infecting a host cell. To date, the retroviral vectors are amongst the most widely used and their mode of infection is widely described in the literature accessible to the person skilled in the art.

The principle of gene therapy is to deliver a functional gene, called a gene of interest, of which the RNA or the corresponding protein will produce the desired biochemical effect in the targeted cells or tissues. On the one hand, the insertion of genes allows the prolonged expression of complex and unstable molecules such as RNAs or proteins which can be extremely difficult or even impossible to obtain or to administer directly. On the other hand, the controlled insertion of the desired gene into the interior of targeted specific cells allows the expression product to be regulated in defined tissues. For this, it is necessary to be able to insert the desired therapeutic gene into the interior of chosen cells and thus to have available a method of insertion capable of specifically targeting the cells or the tissues chosen.

Among the methods of insertion of genes, such as, for example, microinjection, especially the injection of naked plasmid DNA (Derse, D. et al., 1995, and Zhao, T. M. et al., 1996), electroporation, homologous recombination, the use of viral particles, such as retroviruses, is widespread. However, applied in vivo, the gene transfer systems of recombinant retroviral type at the same time have a weak infectious power (insufficient concentration of viral particles) and a lack of specificity with regard to chosen target cells.

The production of cell-specific viral vectors, having a tissue-specific tropism, and whose gene of interest can be translated adequately by the target cells, is realizable, for example, by fusing a specific ligand of the target host cells to the N-terminal part of a surface protein of porcine parainfluenza virus 1. It is possible to mention, for example, the construction of retroviral particles having the CD4 molecule on the surface of the envelope so as to target the human cells infected by the HIV virus (YOUNG, J. A. T. et al., Sciences 1990, 250, 1421-1423), viral particles having a peptide hormone fused to an envelope protein to specifically infect the cells expressing the corresponding receptor (KASAHARA, N. et al., Sciences 1994, 266, 1373-1376) or else alternatively viral particles having a fused polypeptide capable of immobilizing on the receptor of the epidermal growth factor (EGF) (COSSET, F. L. et al., J. of Virology 1995, 69, 10, 6314-6322). In another approach, single-chain fragments of antibodies directed against surface antigens of the target cells are inserted by fusion with the N-terminal part of the envelope protein (VALSESIA-WITTMAN, S. et al., J. of Virology 1996, 70, 3, 2059-2064; TEARINA CHU, T. H. et al., J. of Virology 1997, 71, 1, 720-725).

For the purposes of the present disclosure, a gene of interest in use in the disclosure can be obtained from a eukaryotic or prokaryotic organism or from a virus by any conventional technique. It is, preferably, capable of producing an expression product having a therapeutic effect and it can be a product homologous to the cell host or, alternatively, heterologous. In the scope of the present disclosure, a gene of interest can code for an (i) intracellular or (ii) membrane product present on the surface of the host cell or (iii) secreted outside the host cell. It can therefore comprise appropriate additional elements such as, for example, a sequence coding for a secretion signal. These signals are known to the person skilled in the art.

In accordance with the aims pursued by the present disclosure, a gene of interest can code for a protein corresponding to all or part of a native protein as found in nature. It can likewise be a chimeric protein, for example arising from the fusion of polypeptides of various origins or from a mutant having improved and/or modified biological properties. Such a mutant can be obtained, by conventional biological techniques, by substitution, deletion and/or addition of one or more amino acid residues.

It is very particularly preferred to employ a gene of therapeutic interest coding for an expression product capable of inhibiting or retarding the establishment and/or the development of a genetic or acquired disease. A vector according to the disclosure is in particular intended for the prevention or for the treatment of other bacteria or infectious diseases due to a pathogenic organism: virus, bacteria, parasite or prion. The genes of interest utilizable in the present disclosure are those which code, for example, for the following proteins: a cytokine and especially an interleukin, an interferon, a tissue necrosis factor and a growth factor and especially a hematopoietic growth factor (G-CSF, GM-CSF), a factor or cofactor involved in clotting and especially factor VIII, von Willebrand's factor, antithrombin III, protein C, thrombin and hirudin, an enzyme or an enzyme inhibitor such as the inhibitors of viral proteases, an expression product of a suicide gene such as thymidine kinase of the HSV virus (herpesvirus) of type 1, an activator or an inhibitor of ion channels, a protein of which the absence, the modification or the deregulation of expression is responsible for a genetic disease, such as the CFTR protein, dystrophin or minidystrophin, insulin, ADA (adenosine diaminose), glucocerebrosidase and phenylhydroxylase, a protein capable of inhibiting the initiation or the progression of cancers, such as the expression products of tumor suppressor genes, for example the P53 and Rb genes, a protein capable of stimulating an immune or an antibody response, and a protein capable of inhibiting a viral infection or its development, for example the antigenic epitopes of the virus in question or altered variants of viral proteins capable of entering into competition with the native viral proteins.

The disclosure thus relates to the vectors characterized in that they comprise a nucleotide sequence of porcine parainfluenza virus 1 according to the disclosure, and in that they additionally comprise a gene of interest.

The present disclosure likewise relates to viral particles generated from said vector according to the disclosure. It additionally relates to methods for the preparation of viral particles according to the disclosure, characterized in that they employ a vector according to the disclosure, including viral pseudoparticles (VLP, virus-like particles).

The disclosure likewise relates to animal cells transfected by a vector according to the disclosure. Likewise comprised in the disclosure are animal cells, especially mammalian, infected by a viral particle according to the disclosure.

The present disclosure likewise relates to a vector, a viral particle or a cell according to the disclosure, for the treatment and/or the prevention of a genetic disease or of an acquired disease such as cancer or an infectious disease. The disclosure is likewise directed at a pharmaceutical composition comprising, by way of therapeutic or prophylactic agent, a vector or a cell according to the disclosure, in combination with a vehicle acceptable from a pharmaceutical point of view.

Another aspect of the present disclosure provides a method of producing and/or recovering any recombinant PPIV1 protein, including any open reading frame protein, by 1) permitting infection of a number of susceptible cells in culture with a recombinant viral vector, ii) expressing PPIV1 protein by the recombinant viral vector, iii) recovering the expressed PPIV1 protein, and, iv) separating cell debris from the expressed PPIV1 protein via a separation step. In one preferred form, the recombinant viral vector is a baculovirus containing ORF DNA coding sequences and the cells are SF+ cells. Preferred separation steps are known in the art.

As used herein "ORF" refers to any open reading frame present in the PPIV1 genome.

For recovery of PPIV1 ORF that will be used in an immunogenic or immunological composition such as a vaccine, the inclusion of an inactivation step is preferred in order to inactivate the viral vector. An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in severity or incidence or lack of symptoms normally displayed by an infected host, a quicker recovery time, and/or a lowered viral titer in the infected host. Thus, the present disclosure also relates to method of producing and/or recovering recombinant PPIV1 ORF protein, preferably in amounts described above, by i) permitting infection of a number of susceptible cells in culture with a recombinant viral vector, ii) expressing PPIV1 ORF protein by the recombinant viral vector, iii) recovering the PPIV1 ORF, iv) separating cell debris from the expressed PPIV1 ORF via a separation step, and v) inactivating the recombinant viral vector.

In some forms, this inactivation is done either just before or just after the filtration step. Any conventional inactivation method can be used for purposes of the present disclosure. Thus, inactivation can be performed by chemical and/or physical treatments. One representative inactivation method includes the addition of cyclized binary ethylenimine (BEI). After inactivation is completed, a sodium thiosulfate solution is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

Thus, another aspect of the present disclosure relates to a method of producing recombinant PPIV1 ORF protein by i) permitting infection of a number of susceptible cells in culture with a recombinant viral vector, ii) expressing PPIV1 ORF protein by the recombinant viral vector, iii) recovering the PPIV1 ORF, iv) separating cell debris from the expressed PPIV1 ORF via a separation step, and v) inactivating the recombinant viral vector.

Optionally, the method described above may also include a neutralization step after step v). This step vi) comprises adding an equivalent amount of an agent that neutralizes the inactivation agent within the solution. For example, if the inactivation agent is BEI, addition of sodium thiosulfate to an equivalent amount is preferred.

In preferred forms and especially in forms that will use the recombinant PPIV1 ORF protein in an immunogenic composition such as a vaccine, each lot of harvested ORF will preferably be tested for inactivation. Thus a further aspect of the present disclosure relates to an inactivation test for determining the effectiveness of the inactivation of the recombination viral vector, comprising the steps: i) contacting at least a portion of the culture fluid containing the recombinant viral vector with an inactivating agent, ii) adding a neutralization agent to neutralize the inactivation agent, and iii) determining the residual infectivity.

In preferred forms the recombinant viral vector containing PPIV1 ORF DNA and expressing PPIV1 ORF protein used to infect the cells is generated by transfecting a transfer vector that has had an ORF gene cloned therein into a viral vector. Preferably, only the portion of the transfer vector that contains the ORF DNA is transfected into the viral vector. The term "transfected into a viral vector" means, and is used as a synonym for "introducing" or "cloning" a heterologous DNA into a viral vector, such as for example into a baculovirus vector. A "transfer vector" means a DNA molecule, that includes at least one origin of replication, the heterologous gene, in the present case PPIV1 ORF, and DNA sequences which allow the cloning of said heterologous gene into the viral vector. Preferably the sequences which allow cloning of the heterologous gene into the viral vector are flanking the heterologous gene. Even more preferably, those flanking sequences are at least homologous in parts with sequences of the viral vector. The sequence homology then allows recombination of both molecules, the viral vector, and the transfer vector to generate a recombinant viral vector containing the heterologous gene.

In more preferred forms, the methods of the present disclosure will begin with the isolation of PPIV1 ORF DNA. Any PPIV1 ORF gene known in the art can be used for purposes of the present disclosure. The PPIV1 ORF DNA is preferably amplified using PCR methods. The resulting DNA is then cloned into the transfer vector.

Thus, in one aspect of the present disclosure, a method for constructing a recombinant viral vector containing PPIV1 ORF DNA is provided. This method comprises the steps: 1) cloning a recombinant PPIV1 ORF into a transfer vector; and ii) transfecting the portion of the transfer vector containing the recombinant PPIV1 ORF into a viral vector, to generate the recombinant viral vector.

According to a further aspect, this method further comprises prior to step 1) the following step: amplifying the PPIV1 ORF DNA in vitro, wherein the flanking sequences of the PPIV1 ORF DNA are modified. In vitro methods for amplifying the PPIV1 ORF DNA and modifying the flanking sequences, cloning in vitro amplified PPIV1 ORF DNA into a transfer vector and suitable transfer vectors are described above or known to a person skilled in the art. Thus according to a further aspect, the present disclosure relates to a method for constructing a recombinant viral vector containing PPIV1 ORF DNA and expressing PPIV1 ORF protein comprising the steps of: 1) amplifying PPIV1 ORF DNA in vitro, wherein the flanking sequences of said PPIV1 ORF DNA are modified, ii) cloning the amplified PPIV1 ORF DNA into a transfer vector; and iii) transfecting the transfer vector or a portion thereof containing the recombinant PPIV1 ORF DNA into a viral vector to generate the recombinant viral vector. In some aspects, the modification of the flanking sequences of the PPIV1 ORF DNA is performed by introducing a 5' Kozak's sequence and/or an EcoR 1 site.

Optionally, methods of the present disclosure can include the step of amplifying the PPIV1 ORF DNA from a strain of PPIV1 prior to cloning the PPIV1 ORF DNA into the transfer vector. In preferred forms, a 5' Kozak's sequence, a 3' EcoR1 site, and combinations thereof can also be added to the amplified sequence, preferably prior to or during amplification.

A further aspect of the present disclosure relates to a method for preparing a composition comprising PPIV1 ORF protein, and inactivated viral vector. This method generally comprises the steps: i) cloning the amplified PPIV1 ORF into a transfer vector; ii) transfecting the portion of the transfer vector containing the recombinant PPIV1 ORF into a virus; iii) infecting cells in media with the transfected viral vector; iv) causing the transfected viral vector to express the recombinant protein from PPIV1 ORF; v) separating cells from the supernate; vi) recovering the expressed PPIV1 ORF protein; and vii) inactivating the recombinant viral vector.

According to a further aspect, the method for preparing a composition comprising PPIV1 ORF protein, and inactivated viral vector, as described above, also includes a neutralization step after step vii). This step viii) comprises adding an equivalent amount of an agent that neutralizes the inactivation agent within the solution. Preferably, if the inactivation agent is BEI, the addition of sodium thiosulfate to an equivalent amount is preferred. Thus, according to a further aspect, step viii) comprises adding a sodium thiosulfate.

According to a further aspect, the method for preparing a composition comprising PPIV1 ORF protein, and inactivated viral vector, as described above, comprises prior to step i) the following step: amplifying the PPIV1 ORF DNA in vitro, wherein the flanking sequences of the PPIV1 ORF DNA. In vitro methods for amplifying the PPIV1 ORF DNA and modifying the flanking sequences, cloning in vitro amplified PPIV1 ORF DNA into a transfer vector and suitable transfer vectors are known to a person skilled in the art. Thus according to a further aspect, this method comprises the steps: i) amplifying PPIV1 ORF DNA in vitro, wherein the flanking sequences of said PPIV1 ORF DNA are modified, ii) cloning the amplified PPIV1 ORF DNA into a transfer vector; and iii) transfecting the transfer vector or a portion thereof containing the recombinant PPIV1 ORF DNA into a viral vector to generate the recombinant viral vector, iv) infecting cells in media with the transfected virus; v) causing the transfected virus to express the recombinant protein from PPIV1 ORF; vi) separating cells from the supernate; vii) recovering the expressed PPIV1 ORF protein; viii) inactivating the recombinant viral vector; and ix) adding an equivalent amount of an agent that neutralizes the inactivation agent within the solution.

In another aspect of the present disclosure, a method for preparing a composition, preferably an antigenic composition, such as for example a vaccine, for invoking an immune response against PPIV1 is provided. Generally, this method includes the steps of transfecting a construct into a virus, wherein the construct comprises i) recombinant DNA from ORF of PPIV1, ii) infecting cells in growth media with the transfected virus, iii) causing the virus to express the recombinant protein from PPIV1 ORF, iv) recovering the expressed ORF protein, v) and preparing the composition by combining the recovered protein with a suitable adjuvant and/or other pharmaceutically acceptable carrier.

"Adjuvants" as used herein, can include aluminum hydroxide and aluminum phosphate, saponins e.g., Quil A, QS-21 (Cambridge Biotech Inc., Cambridge Mass.), GPI- 0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.). JohnWiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 µg is to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Thus, according to a further aspect, the method for preparing an antigenic composition, such as for example a vaccine, for invoking an immune response against PPIV1 comprises i) preparing and recovering PPIV1 ORF protein, and ii) admixing this with a suitable adjuvant. Preferably, the process step i) includes the process steps as described for the preparation and recovery of PPIV1 ORF. For example, in preferred forms of this method, the construct comprising PPIV1 ORF DNA is obtained in a transfer vector. Optionally, the method may include the step of amplifying the ORF from a strain of PPIV1 through PCR prior to cloning the ORF into the transfer vector. Preferred open reading frame sequences, Kozak's sequences, 3' EcoR1 site sequences, recombinant protein sequences, transfected construct sequences, media, cells, and viruses are known in the art. Another optional step for this method includes cloning the amplified PPIV1 ORF DNA into a first vector, excising the ORF DNA from this first vector, and using this excised PPIV1 ORF DNA for cloning into the transfer vector. Preferably, the recovery step of this method also includes the step of separating the media from the cells and cell debris. This can be done in a variety of ways but for ease and convenience, it is preferred to filter the cells, cell debris, and growth media through a filter having pores ranging in size from about 0.45 µM to about 1.0 µM. Finally, for this method, it is preferred to include a virus inactivation step prior to combining the recovered recombinant PPIV1 ORF protein in a composition.

Thus according to a further aspect, this method comprises the steps: i) amplifying PPIV1 ORF DNA in vitro, wherein the flanking sequences of said PPIV1 ORF DNA are modified, ii) cloning the amplified PPIV1 ORF DNA into a transfer vector; and iii) transfecting the transfer vector or a portion thereof containing the recombinant PPIV1 ORF DNA into a viral vector to generate the recombinant viral vector, iv) infecting cells in media with the transfected virus; v) causing the transfected virus to express the recombinant protein from PPIV1 ORF; vi) separating cells from the supernate; vii) recovering the expressed PPIV1 ORF protein; viii) inactivating the recombinant viral vector; ix) adding of an equivalent amount of an agent that neutralizes the inactivation agent within the solution, and x) adding a suitable amount of an adjuvant preferably in amounts ranging from about 500 µg to about 5 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, protectants including antibacterial and antifungal agents, isotonic agents, adsorption delaying agents, and the like. Stabilizers will be effective at maintaining stability or increasing the shelf life of the composition for a longer period of time than a composition without the stabilizer. Preservatives will increase the shelf life of the composition for a longer period of time than a composition without the preservative. Antibacterial agents will include antibiotics. Most preferably, the composition provided herewith contains PPIV1 ORF protein recovered from in vitro cultured cells, wherein said cells were infected with a recombinant viral vector containing PPIV1 ORF DNA and expressing PPIV1 ORF protein, and wherein said cell culture was treated to inactivate the viral vector, and an equivalent concentration of a neutralization agent was added, and wherein adjuvant and physiological saline is also added.

Thus, a further aspect relates to a method for preparing an antigenic composition, such as for example a vaccine, for invoking an immune response against PPIV1 comprising the steps: i) amplifying PPIV1 ORF DNA in vitro, wherein the flanking sequences of said PPIV1 ORF DNA are preferably modified, ii) cloning the amplified PPIV1 ORF DNA into a transfer vector; and iii) transfecting the transfer vector or a portion thereof containing the recombinant PPIV1 ORF DNA into a viral vector to generate the recombinant viral vector, iv) infecting cells in media with the transfected virus; v) causing the transfected virus to express the recombinant protein from PPIV1 ORF; vi) separating cells from the supernate; vii) recovering the expressed PPIV1 ORF protein; viii) inactivating the recombinant viral vector; ix) adding an equivalent amount of an agent that neutralizes the inactivation agent within the solution; x) adding a suitable amount of an adjuvant; and xi) adding physiological saline, preferably in an amount of about 50 to about 90% (v/v), more preferably to about 60 to 80% (v/v), still more preferably of about 70% (v/v). Optionally, this method can also include the addition of a protectant. A protectant as used herein, refers to an anti-microbiological active agent, such as for example Gentamycin, Merthiolate, and the like. In particular adding a protectant is most preferred for the preparation of a multi-dose composition. Those anti-microbiological active agents are added in concentrations effective to prevent the composition of interest from any microbiological contamination or for inhibition of any microbiological growth within the composition of interest.

Moreover, this method can also comprise the addition of any stabilizing agent, such as for example saccharides, trehalose, mannitol, saccharose and the like, to increase and/or maintain product shelf-life.

A further aspect of the present disclosure relates to the products resulting from the methods as described above. In particular, the present disclosure relates to a composition of matter comprising recombinantly expressed PPIV1 ORF protein. Preferably, this composition of matter also comprises an agent suitable for the inactivation of viral vectors and comprises an agent, suitable for the inactivation of viral vectors.

In yet another aspect of the present disclosure, an immunogenic composition that induces an immune response and, more preferably, confers protective immunity against the clinical signs of PPIV1 infection, is provided. The composition generally comprises the polypeptide, or a fragment thereof, expressed by an Open Reading Frame (ORF) of PPIV1, as the antigenic component of the composition.

Any PPIV1 ORF would be effective as the source of the PPIV1 ORF DNA and/or polypeptide as used herein. A preferred PPIV1 ORF protein is an ORF of SEQ ID NO. 1 or 2, but it is understood by those of skill in the art that this sequence could vary by as much as 10-15% in sequence homology and still retain the antigenic characteristics that render it useful in immunogenic compositions. The antigenic characteristics of an immunological composition can be, for example, estimated by challenge experiments. Moreover, the antigenic characteristic of a modified antigen is still retained, when the modified antigen confers at least 70%, preferably 80%, more preferably 90% of the protective immunity as compared to a PPIV1 ORF protein, encoded by the ORF polynucleotide sequence of SEQ ID NO:1 or 2.

An "immunogenic composition" as used herein, means a PPIV1 component which elicits an "immunological response" in the host of a cellular and/or antibody-mediated immune response to PPIV1 component. Preferably, this immunogenic composition is capable of conferring protective immunity against PPIV1 infection and the clinical signs associated therewith. In some forms, immunogenic portions of PPIV1 ORF protein are used as the antigenic component in the composition and in some other forms, PP1V1 DNA is used. The term "immunogenic portion" as used herein refers to truncated and/or substituted forms, or fragments of PPIV1 ORF protein and/or polynucleotide, respectively. Preferably, such truncated and/or substituted forms, or fragments will comprise at least 6 contiguous amino acids from the full-length ORF polypeptide. More preferably, the truncated or substituted forms, or fragments will have at least 10, more preferably at least 15, and still more preferably at least 19 contiguous amino acids from the full-length ORF polypeptide. It is further understood that such sequences may be a part of larger fragments or truncated forms. Preferably, such truncated or substituted forms, or fragments will comprise at least 18 contiguous nucleotides from a full-length ORF nucleotide sequence, e.g. an ORF of SEQ ID NO: 1. More preferably, the truncated or substituted forms, or fragments will have at least 30, more preferably at least 45, and still more preferably at least 57 contiguous nucleotides a full-length ORF nucleotide sequence, e.g. an ORF of SEQ ID NO: 1.

Thus, a further aspect of the present disclosure relates to an immunogenic composition effective for lessening the severity of clinical symptoms associated with PPIV1 infection comprising PPIV1 ORF protein. Preferably, the PPIV1 ORF protein is:
i) a polypeptide comprising an ORF encoded by the sequence of SEQ ID NO: 1 or 2;
ii) any polypeptide that is at least 80% homologous to the polypeptide of i);
iii) any immunogenic portion of the polypeptides of i) and/or ii);
iv) the immunogenic portion of iii), comprising at least 10 contiguous amino acids included in the sequences of an ORF of SEQ ID NO: 1 or 2;
v) a polypeptide that is encoded by a polynucleotide comprising an ORF of sequence of SEQ ID NO: 1 or 2;
vi) any polypeptide that is encoded by a polynucleotide that is at least 80% homologous to the polynucleotide of v);
vii) any immunogenic portion of the polypeptides encoded by the polynucleotide of v) and/or vi); or
viii) the immunogenic portion of vii), wherein the polynucleotide coding for said immunogenic portion comprises at least 30 contiguous nucleotides included in the sequences of SEQ ID NO: 1 or 2.

Preferably any of those immunogenic portions will have the immunogenic characteristics of PPIV1 ORF protein that is encoded by the ORF of sequence of SEQ ID NO: 1 or 2.

According to a further aspect, PPIV1 ORF protein is provided in the immunological composition at an antigen inclusion level effective for inducing the desired immune response, namely reducing the incidence of or lessening the severity of clinical signs resulting from PPIV1 infection. Preferably, the PPIV1 ORF protein inclusion level is at least 0.2 μg antigen/ml of the final immunogenic composition (μg/ml), more preferably from about 0.2 to about 400 μg/ml.

The PPIV1 ORF polypeptide used in an immunogenic composition in accordance with the present disclosure can be derived in any fashion including isolation and purification of PPIV1 ORF, standard protein synthesis, and recombinant methodology. Preferred methods for obtaining PPIV1 ORF polypeptide are described herein. Briefly, susceptible cells are infected with a recombinant viral vector containing PPIV1 ORF DNA coding sequences, PPIV1 ORF polypeptide is expressed by the recombinant virus, and the expressed PPIV1 ORF polypeptide is recovered by filtration and inactivated by any conventional method.

Thus, according to a further aspect the immunogenic composition comprises i) any of the PPIV1 ORF proteins described above, preferably in concentrations described above, and ii) at least a portion of the viral vector expressing said PPIV1 ORF protein. Moreover, according to a further aspect, the immunogenic composition comprises i) any of the PPIV1 ORF proteins described above, preferably in concentrations described above, ii) at least a portion of the viral vector expressing said PPIV1 ORF protein, and iii) a portion of the cell culture supernate.

According to a further aspect, the present disclosure relates to an immunogenic composition that comprises i) any of the PPIV1 ORF protein described above, preferably in concentrations described above, ii) at least a portion of the viral vector expressing said PPIV1 ORF protein, iii) a portion of the cell culture, iv) and inactivating agent to inactivate the recombinant viral vector, wherein about 90% of the components i) to iii) have a size smaller than 1 μm.

According to a further aspect, the present disclosure relates to an immunogenic composition that comprises i) any of the PPIV1 ORF proteins described above, preferably in concentrations described above, ii) at least a portion of the viral vector expressing said PPIV1 ORF protein, iii) a portion of the cell culture, iv) an inactivating agent to inactivate the recombinant viral vector, and v) an neutralization agent to stop the inactivation mediated by the inactivating agent, wherein about 90% of the components i) to iii) have a size smaller than 1 μm.

The polypeptide is incorporated into a composition that can be administered to an animal susceptible to PPIV1 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

In a preferred embodiment, the immunogenic composition comprises PPIV1 ORF protein as provided herewith, preferably in concentrations described above as an antigenic component, which is mixed with an adjuvant and physiological saline.

Those of skill in the art will understand that the composition herein may incorporate known injectable, physiologically acceptable, sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants, are those described above.

Thus, the present disclosure also relates to an immunogenic composition that comprises i) any of the PPIV1 ORF proteins described above, preferably in concentrations described above, ii) at least a portion of the viral vector expressing said PPIV1 ORF protein, iii) a portion of the cell culture, iv) an inactivating agent to inactivate the recombinant viral vector, and v) a neutralization agent to stop the inactivation mediated by the inactivating agent; and vi) a suitable adjuvant in amounts described above; wherein about 90% of the components i) to iii) have a size smaller than 1 μm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic compositions can further include one or more other immunomodulatory agents such as, e. g., interleukins, interferons, or other cytokines. The immunogenic compositions can also include Gentamicin and Merthiolate. While the amounts and concentrations of adjuvants and additives useful in the context of the present disclosure can readily be determined by the skilled artisan, the present disclosure contemplates compositions comprising from about 50 μg to about 2000 μg of adjuvant and preferably about 250 μg/ml dose of the vaccine composition. In another preferred embodiment, the present disclosure contemplates vaccine compositions comprising from about 1 ug/ml to about 60 μg/ml of antibiotics, and more preferably less than about 30 μg/ml of antibiotics.

Thus, the present disclosure also relates to an immunogenic composition that comprises i) any of the PPIV1 ORF proteins described above, preferably in concentrations described above, ii) at least a portion of the viral vector expressing said PPIV1 ORF protein, iii) a portion of the cell culture, iv) an inactivating agent to inactivate the recombinant viral vector, and v) an neutralization agent to stop the inactivation mediated by the inactivating agent; vi) a suitable adjuvant in amounts described above; vii) a pharmaceutical acceptable concentration of a saline buffer, preferably of a phosphate salt, and viii) an anti-microbiological active agent; wherein about 90% of the components i) to iii) have a size smaller than 1 μm.

It will be found that the immunogenic compositions comprising recombinant PPIV1 ORF protein as provided herewith are very effective in reducing severity of or incidence of the clinical symptoms associated with PPIV1 infections. Clinical symptoms will include one or more of respiratory symptoms similar to influenza or PRRSV, decreased appetite, decrease rate of weight gain, weight loss, and slower weaning.

A further aspect relates to a container comprising at least one dose of the immunogenic composition of PPIV1 ORF protein as provided herewith, wherein one dose comprises at least 2 μg PPIV1 ORF protein. Said container can comprise from 1 to 250 doses of the immunogenic composition, preferably it contains 1, 10, 25, 50, 100, 150, 200, or 250 doses of the immunogenic composition of PPIV1 ORF protein. Preferably, each of the containers comprising more than one dose of the immunogenic composition of PPIV1 ORF protein further comprises an anti-microbiological active agent. Those agents are for example, antibiotics including Gentamicin and Merthiolate and the like. Thus, one aspect of the present disclosure relates to a container that comprises from 1 to 250 doses of the immunogenic composition of PPIV1 ORF protein, wherein one dose comprises at least 2 μg PPIV1 ORF protein, and Gentamicin and/or Merthiolate, preferably from about 1 µg/ml to about 60 µg/ml of antibiotics, and more preferably less than about 30 µg/ml.

A further aspect relates to a kit, comprising any of the containers, described above, and an instruction manual, including the information for the intramuscular application of at least one dose of the immunogenic composition of PPIV1 ORF protein into piglets to lessen the severity of clinical symptoms associated with PPIV1 infection. Moreover, according to a further aspect, said instruction manual comprises the information of a second or further administration(s) of at least one dose of the immunogenic composition of PPIV1 ORF, wherein the second administration or any further administration is at least 14 days beyond the initial or any former administration. Preferably, said instruction manual also includes the information, to administer an immune stimulant. Preferably, said immune stimulant shall be given at least twice. Preferably, at least 3, more preferably at least 5, and even more preferably at least 7 days are between the first and the second or any further administration of the immune stimulant. Preferably, the immune stimulant is given at least 10 days, preferably 15, even more preferably 20, and still even more preferably at least 22 days beyond the initial administration of the immunogenic composition of PPIV1 ORF protein. It is understood that any immune stimulant known to a person skilled in the art can also be used. "Immune stimulant" as used herein, means any agent or composition that can trigger a general immune response, preferably without initiating or increasing a specific immune response, for example the immune response against a specific pathogen. It is further instructed to administer the immune stimulant in a suitable dose. Moreover, the kit may also comprise a container, including at least one dose of the immune stimulant.

A further aspect of the present disclosure relates to the kit as described above, comprising the immunogenic composition of PPIV1 ORF as provided herewith and the instruction manual, wherein the instruction manual further includes the information to administer the PPIV1 ORF immunogenic composition together, or around the same time as, with an immunogenic composition that comprises an additional antigen effective for reducing the severity of or incidence of clinical signs related to another porcine pathogen. Preferably, the manual contains the information of when the PPIV1 ORF containing composition and the immunogenic composition that comprises an additional antigen are administered.

A further aspect, relates to the use of any of the compositions provided herewith as a medicament, preferably as a veterinary medicament, even more preferably as a vaccine. Moreover, the present disclosure also relates to the use of any of the compositions described herein, for the preparation of a medicament for lessening the severity of clinical symptoms associated with PPIV1 infection. Preferably, the medicament is for the prevention of a PPIV1 infection, even more preferably in piglets.

A further aspect relates to a method for (i) the prevention of an infection, or re-infection with PPIV1 or (ii) the reduction or elimination of clinical symptoms caused by PPIV1 in a subject, comprising administering any of the immunogenic compositions provided herewith to a subject in need thereof. Preferably, the subject is a pig. Preferably, one dose or two doses of the immunogenic composition is/are administered, wherein one dose preferably comprises at least about 2 µg PPIV1 ORF protein. A further aspect relates to the method of treatment as described above, wherein a second application of the immunogenic composition is administered. Preferably, the second administration is done with the same immunogenic composition, preferably having the same amount of PPIV1 ORF protein. Preferably, the second administration is done at least 14 days beyond the initial administration, even more preferably at least 4 weeks beyond the initial administration.

According to a further aspect, the method of treatment also comprises the administration of an immune stimulant. Preferably, said immune stimulant is administered at least twice. Preferably, at least 3, more preferably at least 5 days, even more preferably at least 7 days are between the first and the second administration of the immune stimulant. Preferably, the immune stimulant is administered at least 10 days, preferably 15, even more preferably 20, still more preferably at least 22 days beyond the initial administration of the PPIV1 ORF immunogenic composition. It is within the general knowledge of a person skilled in the art to administer the immune stimulant in a suitable dose.

According to a further aspect, the present disclosure provides a multivalent combination vaccine which includes an immunological agent effective for reducing the incidence of or lessening the severity of PPIV1 infection, and at least one immunogenic active component against another disease-causing organism in swine.

In particular the immunological agent effective for reducing the incidence of or lessening the severity of PPIV1 infection is a PPIV1 antigen. Preferably, said PPIV1 antigen is a PPIV1 ORF protein as provided herewith, or any immunogenic composition as described above, that comprises PPIV1 ORF protein.

However it is herewith understood, that a PPIV1 antigen also refers to any composition of matter that comprises at least one antigen that can induce, stimulate or enhance the immune response against PPIV1 infection, when administered to a pig. In some forms, said PPIV1 antigen is the whole PPIV1 virus, preferably in an inactivated form, a live modified or attenuated PPIV1 virus, a chimeric virus that comprises at least an immunogenic amino acid sequence of PPIV1, any other polypeptide or component that comprises at least an immunogenic amino acid sequence of PPIV1. It is understood that any ORF of PPIV1 can be used for purposes of the present invention. Multiple ORFs of PPIV1 may be used for purposes of the immunogenic composition. The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. An "immunogenic protein", "immunogenic polypeptide" or "immunogenic amino acid sequence" as used herein, includes the full-length sequence of any proteins, analogs thereof, or immunogenic fragments thereof. By "immunogenic fragment" is meant a fragment of a protein which includes one or more epitopes and thus elicits the immunological response against the relevant pathogen. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986)

Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, June 28-Jul. 3, 1998.

Preferably the other disease-causing organism in swine is selected from the group consisting of: *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Ci. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (M hyo); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Vesicular stomatitis virus; Virus of vesicular exanthema of swine; *Leptospira hardjo*; and/or *Mycoplasma hyosynoviae*.

An "immunological active component" as used herein means a component that induces or stimulates the immune response in an animal to which said component is administered. According to a preferred embodiment, said immune response is directed to said component or to a microorganism comprising said component. According to a further preferred embodiment, the immunological active component is an attenuated microorganism, including modified live virus (MLV), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. According to a preferred embodiment, said immune response is directed to said immunological active part of a microorganism or to a microorganism comprising said immunological active part.

Formulations

An important aspect of the present disclosure is the preparation of the combination vaccine(s). The skilled person knows additional components which may be comprised in said composition (see also Remington's Pharmaceutical Sciences. (1990). 18th ed. Mack Publ., Easton). The expert may use known injectable, physiologically acceptable, sterile solutions. For preparing a ready-to-use solution for parenteral injection or infusion, aqueous isotonic solutions, such as e.g. saline or corresponding plasma protein solutions, are readily available. The pharmaceutical compositions may be present as lyophylisates or dry preparations, which can be reconstituted with a known injectable solution directly before use under sterile conditions, e.g. as a kit of parts.

In addition, the immunogenic and vaccine compositions of the present disclosure can include one or more veterinary-acceptable carriers. As used herein,"a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

Preferred adjuvants are those as described above. The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present disclosure can readily be determined by the skilled artisan, the present disclosure contemplates compositions comprising from about 50 ug to about 2000 ug of adjuvant and preferably about 250 ug/ml dose of the vaccine composition. In another preferred embodiment, the present disclosure contemplates vaccine compositions comprising from about 1 ug/ml to about 60 ug/ml of antibiotics, and more preferably less than about 30 ug/ml of antibiotics.

According to a further embodiment the combination vaccine is first dehydrated. If the composition is first lyophilized or dehydrated by other methods, then, prior to vaccination, said composition is rehydrated in aqueous (e.g. saline, PBS (phosphate buffered saline)) or non-aqueous solutions (e.g. oil emulsion (mineral oil, or vegetable/metabolizable oil based/single or double emulsion based), aluminum-based, carbomer based adjuvant).

Dosage and Administration

According to the present disclosure, an effective amount of a combination vaccine administered to pigs provides effective immunity against microbiological infections caused by PPIV1 and at least one further pathogen as listed above. Preferred combinations of antigens for the treatment and prophylaxis of microbiological diseases in pigs are listed above.

According to a further embodiment, the combination vaccine is administered to pigs in one or two doses at an interval of about 2 to 4 weeks. For example, the first administration is performed when the animal is about 2 to 3 weeks to about 8 weeks of age. The second administration is performed about 1 to about 4 weeks after the first administration of the first vaccination. According to a further embodiment, revaccination is performed in an interval of 3 to 12 month after administration of the second dose. Administration of subsequent vaccine doses is preferably done on a 6 month to an annual basis. In another preferred embodiment, animals vaccinated before the age of about 2 to 3 weeks should be revaccinated. Administration of subsequent vaccine doses is preferably done on an annual basis.

The amount of combination vaccine that is effective depends on the ingredients of the vaccine and the schedule of administration. Typically, when an inactivated virus or a modified live virus preparation is used in the combination vaccine, an amount of the vaccine containing about $10^2$ to about $10^9$ TCID$_{50}$ per dose, preferably about $10^3$ to about $10^8$ TCID$_{50}$ per dose, more preferably, about $10^4$ to about $10^8$ TCID$_{50}$ per dose. In general, inactivated antigen is normally used in higher amounts than live modified viruses. Typically, when bacterial antigen is used in the combination vaccine, the vaccine containing an amount of about $10^3$ to about $10^9$ colony forming units (CFU) per dose, preferably, about $10^4$ to about $10^8$ (CFU) per dose, more preferably about $10^5$ to about $10^6$ (CFU) per dose. Sub-unit vaccines are normally administered with an antigen inclusion level of at least 0.2 μg antigen per dose, preferably with about 0.2 to about 400 μg/dose, still more preferably with about 0.3 to about 200 μg/dose, even more preferably with about 0.35 to about 100 μg/dose, still more preferably with about 0.4 to about 50 μg/dose, still more preferably with about 0.45 to about 30 μg/dose, still more preferably with about 0.6 to about 15 μg/dose, even more preferably with about 0.75 to about 8 μg/dose, even more preferably with about 1.0 to about 6 μg/dose, and still more preferably with about 1.3 to about 3.0 μg/dose. For example, the antigen inclusion level of the PPIV1 ORF antigen, preferably of the PPIV1 ORF protein as provided herewith, contains about 2 μg to about 150 μg, preferably about 2 μg to about 60 μg, even more preferably about 2 μg to about 50 μg, even more preferably about 2 μg to about 40 μg, even more preferably about 2 μg to about 30 μg, even more preferably about 2 μg to about 25 μg, even more preferably about 2 μg to about 20 μg, even more preferably about 4 μg to about 20 μg, and even more preferably about 4 μg to about 16 μg. In the case of combination vaccines that include (37), it is preferred to use at least 1 to 10 logs, more preferably, 5-10 logs, and most preferably, 6-8 logs. In the case of combination vaccines that include (41), it is preferred to use at least 1 to 10 logs, more preferably, 3-10 logs, and most preferably, 5-6 logs.

The composition according to the disclosure may be applied intradermally, intratracheally, or intravaginally. The composition preferably may be applied intramuscularly or intranasally. In an animal body, it can prove advantageous to apply the pharmaceutical compositions as described above via an intravenous injection or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the disclosure may be administered once or several times, also intermittently, for instance on a daily basis for several days, weeks or months, and in different dosages.

Methods for Treatment

Yet another important embodiment of the disclosure is a method for the prophylaxis or treatment of diseases caused by PPIV1, and one or more swine pathogenic microorganism(s), wherein a PPIV1 antigen, preferably a PPIV1 ORF protein as provided herewith, and further immunological active components effective for the treatment and/or prophylaxis of the infection caused by said further swine pathogenic microorganism is administered to an animal in need thereof at a suitable dosage. According to a further aspect, said PPIV1 ORF protein, is part of an antigenic composition, as described above. Thus, yet another aspect of the present disclosure relates to a combination vaccine that comprises any one of the antigenic compositions provided herewith and that comprises PPIV1 ORF protein, and another immunological active component effective for the treatment and/or prophylaxis of an infection caused by said other swine pathogenic microorganism.

EXAMPLES

This example illustrates the PPIV1 sequences used in the present disclosure.

Materials and Methods

Collection of samples. Metagenomic sequencing was performed on a pool of two nasal swabs originating from a commercial swine operation in Oklahoma. The samples were submitted to KSVDL from 10-21 day old pigs with acute respiratory disease and had previously tested positive by quantitative reverse transcription polymerase chain reaction (qRT-PCR) for PPIV1 at ISUVDL. Furthermore, these nasal swabs tested negative for influenza A virus (IAV) at ISUVDL. In addition, samples from four pigs with acute respiratory disease were collected from a commercial swine farm in Illinois. A total of 279 porcine nasal swab, oral fluids or lung homogenate samples submitted to ISUVDL for diagnostic testing were screened for the presence of PPIV1 using a qRT-PCR targeting the N gene. The serum samples used for serology were submitted to ISUVDL for porcine reproductive and respiratory syndrome virus (PRRSV) qRT-PCR testing. The serum samples for serology were obtained from eight states: Iowa (n=18), North Carolina (n=6), Nebraska (n=6), Missouri (n=1), Oklahoma (n=6), Minnesota (n=1), Indiana (n=1), Illinois (n=2), Mexico (n=5) and unknown (n=14). Sera (n=18) were also obtained from 3-week old pigs from a specific pathogen free research herd and used as negative controls.

Metagenomic Sequencing. Metagenomic sequencing was performed as previously described (Hause et al., 2015b; Neill et al., 2014). Nasal swab samples were pooled and treated with nucleases at 37° C. for 90 minutes to enrich for viral genetic material. Viral nucleic acids were extracted using the MinElute Virus spin filter kit (Qiagen, Valencia, Calif.) according to the manufacturer's instructions. Synthesis of the first-strand cDNA from viral RNA was performed using the Superscript III first-strand synthesis kit as specified by the manufacturer with previously described primers (Allander et al., 2005). Second strand synthesis was completed with Sequenace 2.0 DNA polymerase followed by cDNA purification using the Agencourt AMPure XP beads using the suggested protocol size selection >300 bp. The double stranded cDNA was amplified with TaKaRa DNA polymerase primers identical those used for first strand synthesis but lacking the random hexamer. A second round of size selection and purification was performed using the Agentcourt AMPure XP beads again selecting for products >300 bp. Amplicons were quantified using a Qubit fluorimeter and libraries were prepared by the standard Nextera XT library preparation kit protocol. Libraries were pooled and sequenced using paired 150 bp reads on an Illumina Miseq instrument.

Data Analysis. Raw sequence reads were parsed based on barcodes incorporated during library preparation and imported into CLC Genomics Workbench (CLC Bio version 7.0). Reads were mapped to the host genome (*Sus scrofa*) and from the unmapped reads, contigs were assembled de novo. Contigs were analyzed by BLASTN. PPIV1 genomes were assembled using a reference based assembler with the S119N strain of PPIV1 as a reference (GenBank JX857411). Sequences were aligned using ClustalW and phylogenetic trees were constructed using MEGA 6.06 software using the maximum-likelihood method with topology verified by 1000 bootstrap replicates (Tamura et al., 2013).

RT-PCR for PPIV1 HN. Viral RNA was isolated using the MagMax-96 total nucleic acid isolation according to manufacturer's instructions. To determine the presence of PPIV1 in samples, a 5'-nuclease assay was designed targeting the N gene: probe, 5'-FAM-AGC AGA GGA GAT GGG AAA CAA CCA (SEQ ID No. 3)-Iowa Black-3'; Forward, 5'-CGG ATA CTT CAT CGT CAG TGT T-3'(SEQ ID No. 4); Reverse, 5'-TGG AGA CAA CAA AGG GAG AAT AG-3' (SEQ ID No. 5). Quantitative RT-PCR using the Qiagen Quantitect RT-PCR kit with the following conditions: 50° C., 30 minutes; 95° C., 15 minutes; and 45 cycles of 94° C., 15 seconds and 60° C. for 60 seconds. The specificity of the assay was verified using samples positive for PPIV1 by metagenomic sequencing and common swine respiratory viruses, IAV and PRRSV. To investigate PPIV1 genetic diversity, 1976 bp fragment of the HN gene was amplified using forward primer 1: 5'-TTA GGG TGC ACG ACA GTA AC-3' (SEQ ID NO. 6) and reverse primer 1: 5'-GTC CAC AGG TCA CTT ATC-3' (SEQ ID No. 7) or forward primer 2: 5'-TTA GGG TGC ACG ACA GTA ACT C-3' (SEQ ID No. 8) and reverse primer 2: 5'-CCA CAG ATC ACC TGT CTC TAA G-3' (SEQ ID No. 9) which amplified a 1873 bp fragment. PCR products were sequenced by Sanger methodology using forward and reverse primers utilized for PCR. Sequencing of the HN gene fragment derived from HN primer set 2 required additional primers: 5'-CGG TGA GAA AGG ATG A-3'(SEQ ID No. 10) and 5'-CAA AGG GTC CTC TAG AAG-3' (SEQ ID No. 11). The RT-PCR was performed using the Superscript III One-Step RT-PCR kit with Platinum Taq with the HN primers and probes as follows: 45° C., 30 minutes; 94° C., 2 minutes; followed by 40 cycles of 94° C., 15 seconds; 55° C., 30 seconds; and 68° C. for 30 seconds.

Virus Isolation. Virus isolation was attempted on swine testicle cells (ST), porcine alveolar macrophages (PAM), primary porcine kidney cells (PK-15) and African green monkey kidney cells (Vero). Cell lines were maintained in minimal essential media (MEM) supplemented with L-glutamine and 5% fetal bovine sera. Porcine kidneys, sourced from an abattoir, were purchased from Innovative Research. Primary porcine kidney cells were cultured by treatment of finely minced kidneys with 0.25% trypsin at 37° C. for 4 hours following transfer to cell culture flasks with MEM with L-glutamine and 100 units/mL penicillin, 100 µg/mL streptomycin and 0.25 µg/mL amphotericin B. Cell culture fluids were removed from the 12-well plates (>80% confluency) and 25-100 uL of sample (depending on available sample volume) was inoculated into 1 mL of viral replacement media, which consisted of MEM and penicillin-streptomycin solution. Plates were incubated 5 days before being frozen, thawed, and passaged as above to fresh monolayers. Cells were observed daily for cytopathic effects and PPIV1 growth was monitored by qRT-PCR.

Immunocapture PCR. Serological analysis was performed using an immunoprecipitation coupled to PCR detection assay (ICPD) modeled after the luciferase immunoprecipitation system (Burbelo et al., 2009, 2011). To measure antibody titers, 10 µl serum was added to 40 µl buffer A (50 mM Tris, pH 7.5, 100 mM NaCl, 5 mM $MgCl_2$, 1% Triton X-100) in a 96-well microtiter polypropylene deep well plate. A pool of PPIV-1 RT-PCR positive nasal swabs (Ct=29.3) served as antigen; 50 µl was added to sample wells on the assay plate and incubated at 1800 rpm for 60 minutes at room temperature. Next, 500 µl of Protein G magnetic Dynabeads® were resuspended in 1 ml of PBST and 10 µl was added to the bottom of each well of the assay plate. The plate was incubated with rotation for 20 minutes at room temperature. After incubation, magnetic beads were captured at the bottom of the wells by incubating the plate for 1 minute on a magnetic plate separator. The plate was washed with 100 µl buffer A, incubated for 1 minute on a plate shaker at 1800 rpm and subsequently captured on the magnet for one minute. The wash liquid was discarded and the plate was washed two more times with buffer A and two times with PBST following the same procedure. After the final wash was discarded, bound antibodies were eluted by the addition of 20 µl of 50 mM Glycine pH 2.8 to each well. The plate was incubated at room temperature on a plate shaker for 2 minutes and captured on the magnetic plate separator. The supernatant was transferred to a clean 96-well plate. The pH was adjusted by adding 30 µl of 1M Tris pH 7.5 and the resulting nucleic acid was purified using the Qiagen MagMax DNA/RNA isolation kit and subsequently tested for PPIV-1 by qRT-PCR.

Recombinant F protein ELISA. A fragment of the PPIV1 F gene encoding amino acids 44-245 was commercially synthesized and cloned into the pET28a (Novagen, Madison, Wis.) vector using the BamHI and XhoI restriction sites. The pET28a-F plasmids were transformed into *E. coli* BL21 (DE3) cells, grown in 2× yeast extract tryptone (YT) medium and induced by the addition of isopropyl β-d-1-thiogalactopyranoside (IPTG). Protein purification was performed using B-PER reagent extraction (Pierce, Rockford, Ill.) followed by Ni-NTA affinity purification using the N-terminal His tag from the pET28 vector. The Ni-NTA agarose (Qiagen, Valencia, Calif.) purification was completed following the manufacturer's instructions. Aliquots of purified protein were stored at −80° C. Recombinant protein purity was assessed by sodium dodecyl sulfate-polyacrylamide gel electrophoresis (SDS-PAGE) under denaturing conditions and stained with Coomassie brilliant blue G-250 (BioRad, Hercules, Calif.). Further verification was performed by Western blot detecting the His-tag at the N-terminal of the recombinant protein. Briefly, protein from the SDS-PAGE gel was transferred to a nitrocellulose membrane (Whatman Piscataway, N.J.) by electroblotting and incubated at room temperature for two hours with anti-Histidine monoclonal antibody (Novagen, Madison, Wis.). The membrane was washed 3× with phosphate saline buffer with 0.05% Tween 20 (PBST) and incubated for 2 hours at room temperature with IRDye 800CW-conjuagted goat anti-mouse antibody (LI-COR Biosciences, Lincoln, Nebr.). The membrane was visualized using a digital imaging system (FLUOstar Omega, microplate reader, BMG Labtech).

The ELISA was performed similar to assays previously described with a few modifications (Hause et al., 2015a; Lin et al., 2005). Briefly, Corning EIA/RIA High-binding plates were coated with 100 ul of 2 ug/ml purified recombinant PPIV-1 F protein diluted in 0.1M sodium carbonate buffer (pH 9.6) and incubated at room temperature for 20 hours. Plates were washed 3× in PBST and 100 µl Starting Block (Thermo Fisher Scientific, Waltham, Mass.) was added to each well. After incubation for 1 hour at 37° C., plates were again washed in PBST. Serum samples were diluted 1:100 in PBST and 100 µl/well was added to the plates. Plates were incubated for 1 hour at 37° C. before being washed 3× with PBST. The goat anti-swine IgG secondary antibody labeled with horseradish peroxidase was diluted to 1:2,000 in PBST and 100 µl was added to each well of the assay plate. Plates were incubated at 37° C. for 1 hour and washed 3× with PBST. Plates were developed using a commercial peroxidase assay kit (ABTS ELISA HRP substrate, KPL, Gaitersburg, Md.) for 10 minutes at room temperature. The reaction was stopped by the addition of stop solution and measure at an absorbance of 405 nm on a microplate reader.

In situ Hybridization (ISH). A viral RNA probe targeting nucleotides 2-1206 of the N gene was synthesized for ISH analysis (Advanced Cell Diagnostics, Hayward, Calif.). The assay was performed on trachea and nasal turbinate tissue samples from the pathogenesis study. The assay was completed as specified by the manufacturer with a few modifications. Three pretreatment steps included Pretreatment 1 for 10 min at room temperature, Pretreatment 2 for 15 min at 100-105° C. and pretreatment 3 for 30 min at 40° C. The RNA probe was added to cover sections on all slides and incubated at 40° C. for 2 hours. The excess liquid was removed and slides were washed 2× in wash buffer at room temperature for 2 minutes. All slides went through six rounds of amplification with washes between each round alternating 30 minutes at 40° C. and 15 minutes at 40° C. Then the chromagen, DAB, was applied for 10 min atroom temperature. Finally, slides were counterstained using Gill #1 hematoxylin for 30 seconds and blued for 5 minutes in running tap water.

Pathogenicity studies in pigs. Eleven three-week old pigs from a farm that was qRT-PCR positive for PPIV1 were transported to the University of Nebraska-Lincoln facility for swine research and allowed to acclimate for four days prior to sampling. Pigs were observed daily for clinical signs of illness such as sneezing, coughing, and nasal discharge. Nasal swabs were collected on days 0, 2, 4, 6, 9, 11, and 14. Blood was collected on day 0 and day 14 for serological analysis. Two pigs were randomly sequentially sacrificed on days 2, 4, 6, and 9. Lungs, trachea and nasal turbinates were collected at necropsy and fixed with 10% buffered formalin before embedding in paraffin. Slides were prepared from tissue blocks and stained with hematoxylin and eosin. Nasal swabs were assessed by qRT-PCR. Serum samples were analyzed for antibodies by ICPD.

Genbank Accession Numbers. The two nearly full genome sequences used in the phylogenetic analysis have been submitted to GenBank under acession numbers KT749882 (1438-1) and KT749883 (3103-1). In addition, the ten PPIV1 HN sequences used for phylogeentic analysis were submitted to GenBank as follows; KT749884 (1438-1), KT749885 (1438-4E1), KT749886 (1438-2E6), KT749887 (1438-4E6), KT749888 (1438-3C11), KT749889 (3103-1), KT749890 (3103-D0A4), KT749891 (3103-D0A7), KT749892 (5031-4) and KT749893 (5031-2). Previously published sequences used for phylogenetic analysis include: Swine parainfluenza virus 3 (SPIV3) EU439428; Bovine parainfluenza virus 3 (BPIV3) NC002161; Human parainfluenza virus 3 (HPIV3) NC001796; Sendai virus (SeV) NC 001552; Human parainfluenza virus 1 (HPIV1) NC003461; Porcine parainfluenza 1 (PPIV1) JX857409, JX857410, and JX 857411.

Results and Conclusions

A commercial swine operation in Oklahoma experiencing recurrent disease in pigs approximately 10-21 days of age with clinical symptoms of a moderate cough, minor sneezing and a serous nasal discharge with unknown etiology submitted nasal swabs to be tested negative for influenza A virus (IAV) and positive for PPIV1 by quantitative reverse transcriptase polymerase chain reaction (qRT-PCR). Samples were transferred to KSVDL and metagenomic sequencing was performed on a pool of two nasal swabs. The MiSeq run generated 8.8 million reads with 1.5 million mapping to the Sus scrofa reference genome. De novo assembly of the remaining host subtracted reads resulted in 4,236 contigs which were analyzed by BLASTN. viruses identified were porcine astrovirus 4, porcine circovirus 2, porcine kobuvirus, porcine stool associated circular virus and PPIV1, all with expectation (E) values of 0. Templated assembly using a PPIV1 reference sequence (JX857411) mapped 51,941 reads encompassing 99% of the PPIV1 genome with an average coverage of 353×.

A commercial swine operation in Illinois with similar clinical symptoms to the farm in Oklahoma submitted two approximately 10 day old pigs for diagnostic testing. Metagenomic sequencing of a nasal turbinate homogenate pool generated 2.9 million reads which, following subtraction of reads Sus scrofa, yielded 134 contigs following de novo assembly. BLASTN analysis identified multiple contigs with highly significant E values to porcine astrovirus 4, porcine kobuvirus, porcine hemagglutinating encephalomyelitis virus and PPIV1. Templated assembly of PPIV1 using JX857411 afforded only ~45% genome coverage.

Asymptomatic pigs from a commercial breeding herd in Nebraska that were qRT-PCR positive for PPIV1 were transferred to UNL to monitor PPIV1 pathogenesis. A pool of nasal swabs were subjected to metagenomic sequencing. Of the 617,736 reads, 17,521 mapped to PPIV1 JX857411, resulting in 99% genome coverage. In addition to PPIV1, analysis of 58 host subtracted, de novo assembled contigs identified porcine astrovirus 4, porcine astrovirus 5, porcine bocavirus 3, porcine bocavirus 5 and a small circular DNA virus most similar to one identified in fur seal feces.

PPIV1 qRT-PCR

To investigate the differences seen in the metagenomic sequencing results, a Taqman qRT-PCR assay was designed to target the N region of the PPIV1 genome. Individual testing of the five nasal swab samples from Oklahoma resulted in cycle threshold (Ct) values of 26.0, 28.1, 31.8, 28.9 and 26.0. A nasal swab pool for use in the serological assay had a Ct value of 29.3. Nasal turbinate, lung and brain homogenates were tested individually from the two pigs from Illinois displaying acute respiratory disease with unknown etiology. Only the nasal turbinate from one pig was positive with a Ct of 20.3. Additionally, nasal swabs were submitted from four pigs with similar clinical symptoms from the same site. All of the nasal swabs were positive for PPIV-1 with Ct values of 26.5, 28.0, 32.6 and 34.9. The nasal swabs were negative for IAV by qRT-PCR.

To assess the prevalence of PPIV1 in porcine samples submitted for diagnostic testing, 279 lung homogenate, oral fluid or nasal swab samples of unknown infection status were screened by qRT-PCR for PPIV-1. Seventeen samples tested positive (6.1%). Of the qRT-PCR positive samples, twelve were nasal swabs, four were oral fluids and one was lung homogenate.

Virus Isolation

Virus isolation was attempted on swine testicle, Vero, porcine alveolar macrophage, and primary porcine kidney cells. No CPE was evident. Viral titers were monitored by the N gene qRT-PCR. Following two passages, all samples were negative by qRT-PCR.

Phylogenetic Analysis

The near full genome sequences determined from the nasal swabs from pigs originating in Oklahoma (strain 1438-1) and Nebraska (3103-1) had 97.7% pairwise identity to each other and 90.0-95.3% identity to three PPIV1 sequences from China at the nucleotide level. An approximate 1760 bp fragment of the HN gene was sequenced from 10 U.S. samples and nucleotide identities ranged from 93.7-99.9% for samples from the U.S. and 85.0-95.5% identity to Chinese PPIV1.

Phylogenetic analysis of the genome sequences found that the two nearly complete U.S. sequences formed a well-supported clade that was most similar to Chinese PPIV1 strains S119N and S206N (FIG. 1a). S033N represented a divergent ancestral PPIV1. The PPIV1 clade was most closely related to a clade consisting of human parainfluenza virus 1 and Sendai virus. Phylogenetic analysis was also performed on the HN gene of the parainfluenza virus samples collected in this study and other members of the genus *Respirovirus* (FIG. 1b). Similar to the phylogeny of the genome sequences, all U.S. HN genes formed a well-supported clade most closely related to Chinese strains S119N and S206N. Strains originating from the same state additionally formed well supported clades and for samples from OK (1438-1, 1438-4E1, 1438-2E6, 1438-4E6, 1438-3C11) and NE (3103-1, 3103-D0A4, 3103-D0A7), little diversity between samples was observed. As seen with the genome sequence phylogeny, strain S033N represented a divergent, ancestral member of PPIV1. The PPIV1 clade was well supported and was most closely related to a clade consisting of HPIV1 and SeV. Phylogenetic analysis of predicted HN amino acid sequences yielded identical topology (data not shown).

Pathogenesis of PPIV-1 in Naturally Infected Pigs

Eleven randomly chosen weaned pigs (18-19 days old) from a farm naturally infected with PPIV-1 were analyzed. Throughout the two week observation period, no clinical symptoms of disease such as coughing, sneezing, nasal discharge or lethargy were observed. Nasal swabs collected on day 0 (22-23 days of age) were positive for PPIV1 for six of the eleven pigs (55%) (Table 1). Three additional pigs shed PPIV1 during the course of the study. The length of time for viral shedding was 2-10 days. Quantitative RT-PCR analysis of lung homogenates showed the presence of virus in the lungs of a single pig (A8, Ct=35.2). Histopathology was examined on lung, trachea and nasal turbinates for eight out of the eleven animals (A4-11). Animals A4, A7, A8, and A9 animals had marked atelectasis in the lung tissues but this pathology is not associated with PPIV1. Animals A4, A7, A8, A9 and A11 displayed a subjective decrease in cilia, goblet cells or both in the trachea. In situ hybridization (ISH) using a probe designed to detect PPIV1 identified virus genetic material in turbinate respiratory epithelial cells (FIG. 2a) and to a lesser extent in the trachea (FIG. 2b) in pig A8. The sole pig positive for ISH (A8) displayed the highest amount of viral shedding at time of euthanasia (Ct=25). Mild lymphoplasmacytic rhinitis was observed for all pigs in the study and is likely a background lesion unrelated to the PPIV1 status.

Serological Analysis Suggests Widespread Infection of PPIV-1 in Swine Herds

Sera collected at day 0 and day 14 of the pathogenesis study was subjected to ICPD serological analysis. All day 0 sera were negative for antibodies to PPIV1 as was the negative control where phosphate buffered saline replaced serum. Additional negative controls consisting of 18 serum samples from age-matched specific pathogen free pigs were also all negative. A positive control consisted of pooled sow sera from the farm in Illinois with recurrent unexplained acute respiratory disease in pigs which tested positive for PPIV1. Of the three pigs bled on day 14 of the study, two (pigs A1 and A3) had a detectable antibody response as determined by ICPD with Ct values of 35.0 and 35.1. Pig A2 failed to seroconvert to PPIV1. PPIV1 antibodies in the same samples were also assayed with an indirect ELISA using a recombinant F protein peptide. Using 18 serum samples from age-matched specific pathogen free pigs, a value of >0.36 $A_{405}$ was determined to be a positive result (3 standard deviations above the mean). All but four of the animals on day 0 of the study were positive for PPIV-1 F antibodies by ELISA. While animals A1 and A3 tested negative at the beginning of the study for PPIV-1 F antibodies by ELISA, over the two week observation period these animals shed PPIV1 and subsequently seroconverted. These results were further verified using the ICPD, with these same animals testing negative on day 0 and positive by day 14 of the study. Pig A2 displayed different serological results as those seen for A1 and A3. Pig A2 tested positive for antibodies on both days 0 and 14 and shed virus during the two week observation period. Increased sensitivity associated with the ELISA assay and presence of waning maternal antibodies could explain the discrepant results for pig A2. This hypothesis is also consistent with the finding of seven of eleven pigs positive on the ELISA at day 0 and subsequent PPIV1 infection.

To investigate the prevalence of PPIV1 antibodies in commercial swine, sixty serum samples collected from at least eight states were subjected to ICPD and ELISA serological analysis. PPIV1 antibodies were confirmed positive in 33 samples (55.0%) by ICPD. These results were similar to the PPIV-1 F ELISA in which 38 samples (63.3%) tested positive for PPIV-1 F antibodies. In conjunction with the 6.1% PPIV1 prevalence determined by qRT-PCR, these data suggest that PPIV1 is prevalent in the U.S. swine herd.

Discussion

A number of novel paramyxoviruses causing outbreaks of lethal disease in livestock and humans have been described in recent decades. Some of these, such as Nipah and Hendra viruses, can cross species barriers and cause disease (Chua et al., 1999; Philbey et al., 1998). For instance, Hendra virus (HeV), thought to have originated in bats, caused an outbreak of fatal disease in horses and humans in Australia, 1994 (Murray et al., 1995; Selvey et al., 1995). Furthermore, in 1998, Nipah virus (NiV), also thought to have originated in bats, caused an outbreak of severe encephalitis and death in pigs and humans who had exposure to pigs in Malaysia (Chadha et al., 2006; Chua et al., 1999).

Paramyxoviruses have also caused disease in pigs in the United States. In the 1980s and 1990s two novel swine paramyxoviruses, Texas-81 (81-19252) and ISU-92 (92-7783), were isolated from an outbreak of respiratory and neurological disease in pigs (Janke et al., 2001). These viruses were later determined to be bovine parainfluenza virus type 3 (BPIV3) (Coelingh et al., 1986; Qiao et al., 2009, 2010). BPIV-3 has also been shown to infect humans (Ben-Ishai et al., 1980; Schmidt et al., 2000). Given the propensity of paramyxoviruses for interspecies transmission, further study is warranted, in particular for paramyxoviruses with reservoirs in animals with which humans have frequent contact.

In 2013, a novel paramyxovirus, porcine parainfluenza virus 1, was identified in deceased pigs from a slaughterhouse in Hong Kong, China. No clinical or pathological data were available nor was there information on PPIV1 distribution outside China (Lau et al., 2013). In the present study, we identified PPIV1 in 6% of samples from a collection of acute respiratory disease diagnostic submissions from geographically diverse swine facilities in the United States. Our serological results also support widespread circulation of PPIV1 in the U.S. swine herd, with over 50% of animals having detectable antibodies to PPIV1. It is unclear if PPIV1 is an emerging virus in the U.S. or if it has circulated undetected for some time. Our phylogenetic analysis indicated that the Chinese PPIV1 strain S033N is an ancestor of contemporary U.S. strains and that Chinese strains S206N and S119N had a close sister-clade relationship to U.S. strains. Further genetic analysis of additional genomes, both contemporary and archived, is needed to resolve the evolutionary history of PPIV1. Several swine viruses identified in China have recently emerged in the U.S., including porcine epidemic diarrhea virus and mutant porcine circovirus 2b, illustrating the ease with which swine pathogens can move intercontinentally (Huang et al., 2013; Xiao et al., 2012)

While PPIV1 was detected in nursery-aged pigs with acute respiratory disease in the absence of common etiological agents such as IAV and PRRSV, metagenomic sequencing identified a number of other viruses present in nasal swabs. Porcine astrovirus 4 (PAs4) was identified in all three PPIV1 positive samples analyzed by metagenomic sequencing. PAs4 was previously shown to be commonly detected in swine diarrhea samples in the U.S. (Xiao et al., 2013). PAs4 was also readily identified in both diarrheic and normal swine feces in China (Zhang et al., 2014). An etiologic role for PAs4 in clinical disease has not been established. The two samples from symptomatic pigs were positive for viruses shown to contribute to respiratory disease, porcine circovirus 2 and hemagglutinating encephalomyelitis virus. No clinical symptoms were observed during the course of our pathogenesis study, raising the possibility that PPIV1 infection is asymptomatic without additional cofactors. One difference between our study and PPIV1 positive pigs exhibiting clinical symptoms is the age of pigs. Clinically ill pigs positive for PPIV1 were 10-14 days of age while naturally infected pigs in our studies were approximately 22-26 days of age. Differences in clinical outcomes due to age have previously been seen in swine for viruses such as PEDV (Jung et al., 2015). While our results demonstrate that PPIV1 replicates in respiratory epithelial cells of the upper respiratory tract and exhibits nasal shedding similar to established swine respiratory disease etiologic agents, we were unable to show clinical significance or specific pathological lesions that could have been due to PPIV1 infection.

In addition to PPIV1 identification and characterization, this study developed an innovative method of detecting antibodies using an immunocapture PCR coupled to antigen derived from nasal swabs. This is potentially useful for the large number of novel viruses being discovered which lack in vitro cultivation systems and has the advantage of using native antigen and circumvents potential conformational issues common for recombinant antigens. Further development of this serological method would provide a simple, cheap, and multiplexable method of detection of pathogen exposure in unprocessed animal samples.

I claim:

1. An immunogenic composition comprising:
   a) an antigen of porcine parainfluenza virus 1 (PPIV1);
   b) a pharmaceutically acceptable carrier; and
   c) a component selected from the group consisting of an adjuvant, stabilizer, preservative, or any combination thereof.

2. The immunogenic composition of claim 1, wherein said antigen of PPIV1 is selected from the group consisting of:
   a) a nucleotide sequence selected from SEQ. ID No. 1 or 2;
   b) a polypeptide encoded by the nucleotide sequence of a); and
   c) any combination thereof.

3. The immunogenic composition of claim 2, wherein said nucleotide sequence comprises at least 20 contiguous nucleotides from SEQ ID No. 1 or 2.

4. The immunogenic composition of claim 2, wherein said nucleotide sequence comprises a gene of SEQ ID No. 1 or 2.

5. The immunogenic composition of claim 2, wherein said nucleotide sequence comprises an open reading frame of SEQ ID No. 1 or 2.

6. The immunogenic composition of claim 1, wherein said polypeptide comprises at least 6 contiguous amino acids encoded by SEQ ID No. 1 or 2.

7. The immunogenic composition of claim 6, wherein said polypeptide comprises an expressed gene of SEQ ID No. 1 or 2.

8. The immunogenic composition of claim 6, wherein said polypeptide comprises the protein expressed by an open reading frame of SEQ ID No. 1 or 2.

9. The immunogenic composition of claim 1, wherein both an adjuvant and a stabilizer are included.

10. The immunogenic composition of claim 1, wherein administration of said composition to a pig results in a decrease in severity or incidence of clinical signs associated with or caused by PPIV1 infection.

11. The immunogenic composition of claim 1, wherein said composition includes an antigen from a second disease causing organism in swine that is not PPIV1.

12. The immunogenic composition of claim 11, wherein the PPIV1 antigen and the antigen from said second disease causing organism in swine are combined prior to administration.

13. The immunogenic composition of claim 11, wherein said second disease causing organism in swine is selected from the group consisting of *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cl. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (M hyo); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Vesicular stomatitis virus; Virus of vesicular exanthema of swine; *Leptospira hardjo*; and/or *Mycoplasma hyosynoviae*.

14. A method of decreasing the incidence of or severity of clinical signs associated with infection by PPIV1 in a pig comprising the step of administering the composition of claim 1 to a pig in need thereof.

15. The method of claim 14, wherein said administration occurs before any symptoms of PPIV1 are observed in the pig.

16. The method of claim 14, wherein said composition is administered intravenously, intravascularly, intramuscularly, subcutaneously, intranasally, intraarterially, intraperitoneall, orally, or intrathecally.

17. The method of claim 14, wherein said composition is administered two times.

18. The method of claim 14, wherein a second antigen from a disease causing organism in swine is administered to the pig at the same time as the composition of claim 1.

19. The method of claim 18, wherein the second antigen is combined with said composition.

20. The method of claim 18, wherein said antigen from said second disease causing organism in swine is selected from the group consisting of *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cl. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (M hyo); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Vesicular stomatitis virus; Virus of vesicular exanthema of swine; *Leptospira hardjo*; and/or *Mycoplasma hyosynoviae*.

21. An immunogenic composition comprising:
   a) an antigen of porcine parainfluenza virus 1 (PPIV1);
   b) a pharmaceutically acceptable carrier;
   c) a component selected from the group consisting of an adjuvant, stabilizer, preservative, or any combination thereof; and
   d) an antigen from a second disease causing organism in swine selected from the group consisting of *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus;

*Clostridium* spp., preferably *Cl. difficile, Cl. perfringens* types A, B, and C, *Cl. novyi, Cl. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (M hyo); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Vesicular stomatitis virus; Virus of vesicular exanthema of swine; *Leptospira hardjo*; and/or *Mycoplasma hyosynoviae*.

22. A method of decreasing the incidence of or severity of clinical signs associated with infection by PPIV1 in a pig comprising the steps of:
 administering the composition of claim 1 to a pig in need thereof; and
 administering a second antigen from a disease causing organism in swine to the pig at the same time as the composition of claim 1, wherein said antigen from said second disease causing organism in swine is selected from the group consisting of *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cl. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (M hyo); *Pasteurella multocida*; Porcine cytomegalovirus; Porcine Parvovirus; Porcine Reproductive and Respiratory Syndrome (PRRS) Virus; Pseudorabies virus; Rotavirus; *Salmonella* spp.; preferably *S. thyhimurium*; and *S. choleraesuis; Staph. hyicus; Staphylococcus* spp. preferably *Streptococcus* spp., preferably *Strep. suis*; Swine herpes virus; Swine Influenza Virus; Swine pox virus; Vesicular stomatitis virus; Virus of vesicular exanthema of swine; *Leptospira hardjo*; and/or *Mycoplasma hyosynoviae*.

\* \* \* \* \*

UNITED STATES PATENT AND TRADEMARK OFFICE
CERTIFICATE OF CORRECTION

| | |
|---|---|
| PATENT NO. | : 11,090,378 B2 |
| APPLICATION NO. | : 16/067909 |
| DATED | : August 17, 2021 |
| INVENTOR(S) | : Ben Hause |

It is certified that error appears in the above-identified patent and that said Letters Patent is hereby corrected as shown below:

On the Title Page

Column 1, delete (71) Applicant "Kansas Staten University Research Foundation" and insert therefor -- Kansas State University Research Foundation --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 11

<210> SEQ ID NO 1
<211> LENGTH: 15204
<212> TYPE: DNA
<213> ORGANISM: Porcine Parainfluenza Virus Type 1

<400> SEQUENCE: 1
atcggaggag gtggtggtgc ggttatacct ggacaaaaga acaccgtctc agtatttgtc      60
ctagggtcaa gtattgtaga cgatagcgat aagttagcta tagcactcat gtttttaaca     120
catgctcttg atactgacaa gcaacactca caaagaagcg gtttcctggt ttcattaatg     180
gcaatggcat atagtagtcc tgaattatat ctaacaacaa atggagttaa tgcagatgtt     240
aagtatgtta tctacacaat tgagcatgat ccccagagga caacccataa tgggttcatt     300
gttaggacaa gagatatgga ctatgaaaag acaacagagt ggctattcag ccgtataact     360
aataaatacc cattacttca aggacaaaaa gacactcatg atccagaatc actactccag     420
acttatggat atccctcatg tttaggagca ttgatagtcc aggtttggat tgtcttggtc     480
aaagcaatta caagtagtgc tggattgaag aaaggattct tcaataggct tgaagccttc     540
aggcaggatg gaacagttag aagctcacta gtcttcagtg gagagacagt tgaggggatt     600
gggtcagtga tgagatctca gcagagcctg gtgtccttga tggtagagac tctagttacc     660
atgaacacgg ctagatctga cctgaccact ctagagaaga atattcagat tgttgggaat     720
```

```
tacatcagag atgcaggtct tgcttcattc atgaacacga ttagatatgg tgtagagact    780
aagatggcag cacttacatt atctaatctt agacctgata ttaataaact aaagagttta    840
attgacatct acttatccaa aggtgcaaga gccccttca tatgtatatt acgtgatcca     900
gtacacggaa atttgctcc tggaaattat ccagcattgt ggagttatgc tatgggggtc     960
gcagtagtcc agaacaaagc tatgcagcag tatgtgacag ggaggacata tctggatatg    1020
gaaatgttcc ttcttggtca agcagtagct aaagacgcag atctaagat cagtaatgca     1080 ttagaggatg aattaggtat aactgaaaat gccaaagaca ggctcaaaca tcatcttgct    1140
aacctttctg gaggtgatgg agcctatcat aaacccactg gtggaggagc aatagaagtt    1200
ataattgaca atgcagacat agatctcagg acagaggaaa ccacagaaga atcttcaatc    1260
aggctttcca atattagaga aaacaaaggg agaatagcag acgggcagaa gagatgggaa    1320
acaaccagat ccattggtga tgaccttaat ccagataaca cactgacga tgaagtatcc     1380 gctgcagaaa ggaggattgc agaaagactg gcaaaaaaag agggaaagaa taccaggtcg    1440
gatatactca ttaccgatgg tatgactgaa gatacagata cgatgatga tataatgaga     1500 atgaatgcac taggaggaat ataataaatc aaacaaagg gttttatata ttggttaata    1560
agaaaaactt agggtgaaag aatagctcct agatactagg aactttatca ctcccaaaga   1620
caggatctca aactggccac ccacaaaaga atccctcaaa atccagagac caaatggatc    1680
aggatgccct cttttctgaa gaatctatgg aggatcagaa ggagggacac tcaacaacca    1740
gcacactcac cagtgcagtc ggactcattg acatcatcct tgccagtgag cccacagaca    1800
ttagaaaaga tagaaaacac ctatgtgagc ccatcacagc ttggggaaaa tcagaagcaa    1860
gcaagatttc aagggtaca gtctgtgaag aaaacccaag aacagaaagg gaagattatg     1920
gacaaagtga aaagagtgga attcttaggg agtcaaacaa gtttgaagca gaagtttctt    1980
ttagagaaac tcatagccca gatacatcat ggagggcttg gagaagaagt agtgcagact    2040
ctatacttga gaatatgggc aatggatccg actcctatgg caacgaaatt actgaaaatg    2100
gaggaggaaa ccagagacaa agtcttgaag ctaaagttgg agagatggat ccgagttcta    2160
atacgaggag aaaagacaaa actgagggac ttccagaaga gatacgagga ggttcacccg    2220
tacctaatga cagagaaggt ggaagaaata ataatggagg aagcctggag tctgtcagca    2280
cacataatcc aagagtagaa aataatatta tggatccaac tcatcatctt gaagaagagg    2340
tacttaagag gaacaagcca cgggagatga atgctacaag tcaatggtcg ggtggataca    2400
aggctgatca aaaagacggt aaacatgaat tgataactaa tccagtattt ccaaatcaaa    2460
ataggtcaca gggcacaaaa aaggaaaaag ggaaagaatc agctgtaaag cccaagacca    2520
gaaaatctaa aatgtctttt gaagacacaa gaagcacaga tcacatctac gaagactctc    2580
aagaacatac aagaagaaag aaaacagaca atgaaccatc acaaaagatt ggtaaaaagg    2640
gcacagaaga gaataccta tatacagaag aggtgatcaa attgttagtg agtcttggtg     2700
taatcccatc tgtagccgca ttcaaccaat cccgagacat atgccatgta tttgcaaaac    2760
gtgtcctcaa ttctgtgaac tctgcagaaa tgacagctaa tatgtgcgga ttactgctat    2820
ctgttgagaa atcagtatca gaccggattg aagaaataa gacactaata aatcagatta    2880
taagtgattt aagtataggt agggaagtgc agaaacgttt cactgagtat caaaaggaac    2940
agaattcatt gattatgtca aatctggcga cacttcatat cataacagat agaggaggaa    3000
agaacaacag catggataca ggggagagga ccatcaat caggaccaag gggaaggagc     3060
caacacagag aacacaaaga tttgatccat ctatggaatt caccgaggag attaagtaca    3120
```

```
aacccgatct atacagggaa gacacattga gacaaagaat aacaaaccct gtccttgatg    3180
agagcgcaga gagaatcgac aattcgaatg ccgcgagact gataccttgc aaagaaaaat    3240
caacactgcg ttcactcaaa ctgattattg agagcagcaa tttaagcaga gcagataaaa    3300
ttgcctatat caggtcatta tcaaaatgca aagatgacaa agaggtagaa tcagtaatga    3360
aactatttga ggaagatata gaatcaagta atgaataatc actgatcagc atatccagaa    3420
aatgtcaaga caagagtgta ctgtgatgag taatgactct ccaaataccct aataagaaaa    3480 acttagggtg caagactcac caaccaagcc aagcaaatgg ccgagatcta caagttcccc    3540
aagctatcat acgaggaaca tggatatatg gaacctctac cactaaagac tggcccagat    3600
aagaaggcag tcccacatat aaggataatc aagatagggg acccaccgaa gcatggaaat    3660
cgatatcttg atattctctt acttgggttt tatgagatac ccaaagaagt tggaacatac    3720
ggtagtgtat cagatttgac gagacccacg ggatacacaa tctgcggttc aggatcatta    3780
cctattggaa ttgctaggta cttaggtaca gatcaggaac tactcaaagc atcagtagag    3840
ctaaaggtga cagtgagaag gacagtaaga tcaagtgaga tgattgtgta tatagtagat    3900
tccataccac cagcaatgat ggcttgggct tctaggctga aacgaggcat gatattcaat    3960
gcgaacaaag tagccctagc tcctcaatgt ctacctatag ataaagatat aagattcaga    4020
gttgtctttg tcaatggcac ttctctaggt tctatcacaa tagcaaaagt tcccaagaca    4080
ttagccgatc ttgctttacc gaattccata tcggtcaatt taatggtctc actcaagact    4140
ggtgcgtcaa ctgagtccaa gggcattatt cctacactaa atgaaaaggg tgacaaggta    4200
ttaaacttta tggtacacct cggattaata cataggaaag tcggaagggt gtattcaatg    4260
gagtactgca agggcaaaat agagaagatg cggctgatct tctcattagg actggttgga    4320
ggaatcagtt tccatgttca gcttacaggt gtggtatcta aatcctttgt tggtcagctt    4380
ggagggagaa aggaaatatg ttacccttg atggatgtaa atccacacat gaatttagtt    4440
atctgggctg cttccgttga aatcactggt gtggatgctg ttttccaacc ttccatacca    4500
agagatttca aatactaccc gaatgtggtg gcaaaaaata ttggaaaaat aaaagcttag    4560
agatccaaag ctactgtaac ctcagacatt tcaatattag accggtaagt gtcattatat    4620
gatcagcatc attcatcaga aataagaaaa acttagggta caagttatcc aaaaaagaca    4680
gaacagaaca aacagatcaa gacaagacat cacaaaatgc aaatcatcat cctcagacca    4740
gccataatac taagcatagc actattagtg accagtcaag tccctagaga taaactagcc    4800 aatttagggga tcatcattaa ggacagcaaa gcactcaaaa ttgcaggatc ttatgaaaac    4860
agatacatag tcttaaacct tgtaccaaca atagaaaatg tgaatgggtg tggttccatc    4920
caaatagcaa aatataaaga gatgcttgaa agattgttaa tacctataaa agatgcacta    4980
gatttacaag aatctttgat agtgattgat aatgaaaccg tcaacaacaa ttatcgtcct    5040
cagtatagat ttgtcggtgc aattattggg actatagccc ttggggtagc aactgcggcc    5100
caagttacag caggagtggc tctgatggag gcaagagagg ccaaaagaga tatatcagtg    5160
ttaaaagaag caattggaaa gactcaaaac tcaattgaaa aattacagaa ttctgcaggt    5220
gaacagatac tggctctcaa aatgctccag gattatgtca acgagagat caaaccagct    5280 attgaagaac ttggatgtga gactgctgca cttaaattag gaattgcact tacacaacac    5340
tacacagagc tcaaaatgc ctttgggtcg aatctaggtt ccataggaga aagagctta    5400 acattacagg ccctatcatc attatacaag accaatataa ctgatatact gacaacaact    5460
```

```
aatctcggga aaacagatat ttatgatatt atatatgctg agcaagttaa aggaagagta    5520
atagatgttg atcttagacg atatatggtt acaatatctg taaagatacc aatattatca    5580
gaaataccag gagtattgat ctatgaagtc tcctctatat cttataatat agatggaaca    5640
gagtggtatg ccgctgtacc taaccacata ttaagtaaat ccgcatatat aggggggtgca   5700 gatataagtg attgtataga atctggattg acatatattt gtccgcgaga tcctgctcag    5760
attatagcag ataaccaaca gcaatgtttt ttaggtcatc ttgacaagtg ccctataact    5820
aaagtagttg ataatcttgt gcctaaattt gcattcataa atggtggagt agttgcaaac    5880
tgtatagcct ctacatgtac ctgtggagaa gagagggtcc aggtctctca agatagaaat    5940
aaaggagtaa cctttttgac tcataataat tgtggattaa tagggataaa cgggatggaa    6000
tttcatgcta acaagaaagg gagtgatgct acttggaata tctcccccat aggagtaggg    6060
ccagcagtat cgttaagacc aatagatata tctttacaaa tagtttctgc tactaatttt    6120
ctaaactcat cacgaaaaga tcttatgaag gcaaaagaga tcttaaacca ggtaggaaat    6180
cttagagatt taaccgtcat aacgataatt aatatagtca ttatagctgt attacttata    6240
tgtgtaactg gattaggcgt actgtatcac caattgaaaa gtgcactagt gatgagagac    6300
aagatgtcag tattaaataa tagttcttat tctttagaac caagaaccgc ccaggtacaa    6360
gtaattaagc ctactagttt catgggataa attataaaaa tatattttaa tccatcctca    6420
ttaatcaaag taaagaaaac ttagggtgca cgacagtaat tcaccaccaa aggagaaata    6480
gatcaggaac caacacacta agagatggaa gagaccaaag ttaagacatc agagtactgg    6540
gccaagagtc ctcaaattca cgcaacaaat agtcctaacg tacaaaacag agagaagata    6600
aaggaaacat taacaatttt aatatcattc atttctttcc tatctcttgt actggttata    6660
gctgtactga taatgcaatc tttacataac ggcacaatac taaggtgtaa agatgtaggc    6720
ctagaatcta tcaataaatc cacttactct atatctaatg caattctgga catcatcaaa    6780
caagagctga taactcgtat aataaaatact caaagttctg tgcaggtagc tctcccagtc    6840
ttaattaaca agaaaatcca ggatctctca ctaaccattg agaaaagttc aaaagtgcat    6900
caaaattctc ctacttgtag tggtgtggct gccctgacac atgtggaagg gataaaacct    6960
ttggatccag acgattactg gaggtgtcca agtggggaac catatctaga ggatgaattg    7020
acattaagcc ttatcccagg acctagtatg ctggctggaa cctctaccat tgatggctgt    7080
gtaagattac catcccttgc aataggaaaa tcgctatatg cctatagttc caatcttata    7140
acgaagggtt gtcaagacat agggaaatcc tatcaagtgc tacagttagg tattataact    7200
ctgaattcag acttacatcc cgatttaaat cctataatat cacatactta tgatataaat    7260
gataatagaa agtcctgttc tgttgctgta tcagaaacta aaggatacca attatgctcg    7320
atgccgcgtg tcaatgaaaa aacagattac actagtgatg gtattgaaga tatagttttt    7380
gatgtacttg atctcaaagg gtcctctaga agttttaaat tttcaaacaa tgatataaac    7440
tttgatcatc ctttctcagc gttgtaccct agtgtaggaa gtggtattat atggaaaaat    7500
gaactgtatt tcctaggtta tgggctctg  acaactgcac ttcaagggaa tacaaaatgt    7560
aatttaatgg gatgtccagg agcaacacaa aacaactgta acaagttcat ctctagttca    7620
tggttataca gcaaacagat ggttaatgta ctgatacagg ttaaggggta tttatctaac    7680
aagccaagta ttatagtgag aacaatccca ataacgaaaa attatgtagg agcagaaggg    7740
aaactaatgg gaacacgtga gagaatatat atatatacaa gatcaacggg ttggcatgcc    7800
aatttacaaa taggagtact taatatataa catccaataa ccataacttg gacagatcac    7860
```

```
aaagtactat caagaccagg aagaagtcct tgtgcctgga ataacaaatg ccctagaaat   7920
tgtactactg gtgtatacac agatgcttat cctatatcgc ctgatgctaa ttatgttgct   7980
acagttactc tgttatctaa ttcaacacga actaatccta ctattatgta ttcatcttct   8040
gatagagtat ataatatgtt aagattaaga aatactgaat tagaagctgc atacacaacc   8100
acgtcgtgta ttgtccactt tgatagaggt tattgttttc atattataga aattaatcaa   8160
aaagaactga atacactaca gcctatgctc tttaagactg caattcctaa agcttgcagg   8220
ataagcaatt tataagacac ttattgaaat aataatctgt atctaattac ttaaaagggt   8280
gactgtgcat gacttagaga taagtgatct gtggacataa atcatacagg tcattaatta   8340
gcatataata catctaataa gaaaaactta ggttgaatgc caaagcattc ggccagaatg   8400
gatcatttca atatgtctca aaatccaagt gatatactat accctgaatg ccacttgaac   8460
tctccaattg tgaagggaa gatcgctcag ctacatgtct tgttggatat taatcagccg   8520
tatgaaatga gggaccctag tataatagaa atcatgaaag ttaaaattaa atctggaggg   8580
ttaaatcaaa ggttaatcag aatcagatct ttagggaaag agatgaggag aatcatattt   8640
gattttgata agtatacatt cgaaccttac ccaatatttt ctaaagaatt atttagatta   8700
gagataccag agatttgtga taaaattcaa tcagtttttg cagtgtcgga taagttaagc   8760
aaagatatat cccaaccatt acaatactta tggagagatg tgcgtaggca gttaggaggg   8820
gattgttcca aggatctttc taacaatgag attgatatac acaaaattcc tgaaatccat   8880
actaaattca ccagaaataa ctggtataaa ccattcatga catggtttag tattaaaatat  8940 gatatgagaa gatgtcaaaa gaatagggaa acataaact tagacagtag gcaatcatat   9000
aattatctta actgtaaata ctattttata attatccatc cggatctctt aatgatattg   9060
gacaagatca aatacacggg atacttactg acaccagaat tagtgctaat gtactgtgat   9120
gtggtcgaag gtagatggaa tatgtctgct gctggacaat tagatgacaa atcacacaaa   9180
ataacattga aggagaaga attgtggggc aggatagatg aattattcaa gataatcggg   9240
gaagagacat ttaatatcat atcactattg gagccattat ctttagcatt gatacaatta   9300
acagatcctg ttatgtcttt aaaaggtgca tttatgagac atgtcatctc agaaatgaat   9360
gaaatattgg ttaaatgtgg aaatctaact gaacttgagg tggatcacat aatggattca   9420
atccttaaca ttttttatgga tacaacagta gatgagaaag cagagatatt ctccttcttt   9480
aggacatttg gtcatcctag ccttgaggcc tccatagctg ctgaaaaagt taggcaacat   9540
atgtatgcgc agaaaagtat aaaatataag accttatgtg agtgtcacgc tatattttgt   9600
acaattataa taaacggata tagagacagg cacggaggac aatggccccc ctgtcagttc   9660
ccagatcatg tgtgtcaaga actcagaaat tctcaaggat ctaattcagc tatatcttat   9720
gaaacagccg ttgacaattt cgagagtttt ataggtttca gattcgagaa gttcatagac   9780
cctcaattag atgaagatct cactatttat atgagagata agcattgtc tccaagaaga   9840 gaagcctggg attctgtgta tccagatggc aatctgctat ataaagtgcc gttctctgaa   9900
gaaacaagga gattgataga agtctttatc agtgattcta atttcaatcc agaagacatt   9960
atacaatatg tagagacagg agaatggttg aacgatgata ctttcaacat atcttatagc  10020
ctaaaagaaa aggagatcaa acaagaaggt cgattgtttg ccaagatgac atacaaaatg  10080
agagcagtcc aagtattggc agaaactttg ctagcaaaag gaataggggg tttatttaat  10140
gaaaatggta tggttaaagg tgaaatcgat ttactaaaga gtctaactac tttatctata  10200
```

```
tcaggagttc caaggactag cgagatttat aatgaatcag ttagtgaaga agctgatagg    10260
agaagatggg aaagggaaaa ttcctcatac tattgggaaa aaagaaaaag atcaaaacat    10320
gagttcaaag ccacagactc atctactaac ggctatgaga ctctgagctg ttttcttact    10380
acagacctga agaaatattg tctaaattgg agatttgaga gcacatctct tttcgggcag    10440
agatgtaacg aaatatttgg gttcaagaga ttcttcaact ggatgcatcc tgtattggaa    10500
gaatgtataa tatatgtggg tgatccttac tgtcctgtgc ctgataaaat ccacaagaat    10560
ttagaagatc atgaagattc aggcatcttt atacatagac cgaagggtgg gatagaaggt    10620
tattgtcaaa aactttggac tctcatatct ataagcgcaa ttcatctagc tgctgtcaag    10680
gttggggtta gagtatcagc tatggtacaa ggtgacaacc aagcaattgc cgtaacatct    10740
agggtaccag tgacggccac gtataagttc aaaaaagagc aggtatatac agagatcact    10800
aagtatttta agtctttaag agatgtgatg tctgatttag acatgaact caaactcaac    10860 gagacaatta taagtagcaa gatgttcgtg tatagtaagc ggatatatta tgatggtaaa    10920
atactacccc aatgtttaaa agcacttaca aggtgtgttt tttggtccga gaccttagtg    10980
gatgaaaaca ggtctgcatg ctccaatctt gcaactgcta tagccaaagc tatagaaaat    11040
ggctattcac caatattagg ttactcaata gctctgtata agcttgtca gcaagtatgt    11100 atctcattag ggatgactat caaccctaca ataacaccta atataagaga ccaatattat    11160
ttagggaaga attggcttag atgcgcagtt ttgatacccg ctaatgtagg gggatttaac    11220
tacatggcaa tgtctagatg tttcgtcaga aatataggcg accctgcagt agctgctcta    11280
gcagacctca aaaggtttat ccgagcagga ctattggaca agcaggtttt gtaccgtgta    11340
atgaatcaag aatctgggga gtctaatttc ttagactggg catctgatcc atactcatgt    11400
aatttaccgc actcgcagag tatcacaaca attataaaga atattacagc tcgttcagtt    11460
cttcaagagt caccaaatcc cctactttca ggtttattta catgtgacag taagaagaa    11520 gacttaaatt tagcaacatt tctgatggac aggaaggtca tattgccaag agttgcacat    11580
gagatactag ataactcttt gacagggatc agagaatcta tcgcaggaat gctggacact    11640
acaaaatcat tagtacgggt tagtattagg aaaggggggtt tatcatacaa tctcttaaga    11700
aagctgataa attatgattt attacaatat gaaacattaa ccaggacttt aaggaaagtc    11760
gtcacaaata acattgaata tgaatatatg tgttctgtgg aattagcaat tggattaagg    11820
caaaaaatgt ggtcacatct aacatatggg agacctatac atggattaga aacacctgac    11880
cctctagaac tccttaaagg aacattcatc aaaggatctg aggtttgcaa aatatgcagg    11940
tctgaaggtg ataatcctat atatacttgg ttttatttac ctgaggaaat agatctggat    12000
aacctagaac aaggaaatcc atctataaga ataccttact ttgggtctac tactgacgaa    12060
agatcagaag cacaactggg ttatgttaaa acactgagta aacctgctaa agcagcgatt    12120
aggattgcta tgtatatac ttgggctta ggtactgatg agatatcatg gatggaagcg    12180
gctcagattg cacaaacaag agcaaattta agtcttgata atttgaaact tctgactccg    12240
gtatcaacat ctacaaatct gtctcataga ttaaggaca ctgctaccca gatgaaattc    12300
tcaagtgcaa ctctagttag agctagtaga tttattacta tatcaaatga taagatggct    12360
ctgaaggagg caggtgagac aaaggatact aacttaatat atcagcagat aatgttgaca    12420
ggacttagtg ttttttgaatt caatactaga tacattaaag gtaagactaa acaaccaatg    12480
atactacact tacattaa caatggctgc tgcataatgg aatcaccaca agagacttgt    12540
atccctccta aatctactct agacttagag gtaactaatg aagaaataa attaatatat    12600
```

```
gataataatc cattaaaaaa tgttgatctc ggtattttcc aaaaaattag agatatcgtg    12660
cacactgtag atatgacttt ctggtctgat ttggaaataa tgagagcagt tactatttgt    12720
acatctatga caatagcaga caccatgtct caattggata gagataacct taaagaagta    12780
attgttctta cgaatgatga tgatattaat agcttaataa cagagtttat gataatagat    12840
atcccgctct tttgctcaac attcggagga atcttagtaa atcagtttgc ctatgcatta    12900
tacggtctaa atataagagg tagagaagaa atatggggtt acattacacg gactttgaaa    12960
gatacttctc atgctgtgtt aaaggtactt gctaatgcat tatcacatcc aaaggtgttc    13020
aagagattct gggatttcgg tattttagag cctgtatatg gacctaattt atccaaccaa    13080
gataagataa tgttagcatt atctgtttgt gagtactcaa tagacttatt catgagggac    13140
tggcaaagcg gaatacctct agaaaccttt atatgtgaca atgatccaga agtagttgaa    13200
ttaagaaaag gtgcctactt ggcaagacat ttagcatatt tatgcagctt aggagagatt    13260
tcctcatatg gtcctagatt agaaactcta acatcattag aaaggttaga ggttcttaaa    13320
agctacctag agatatcttg tttagaggat ccaacattga gatacagtca ggttacaggg    13380
cttgtattaa aagtgttccc atcaacagta gtatatatca ggaagttagc tataaagatg    13440
ttgaggatta ggggcatagg ggtgccagag gtgttagaag actgggatcc cagtcatgaa    13500
caagctctac tagataatat agctcaagag attcaacata atatcccaat aaaccaatct    13560
atcaagacac ctttctgggg gctcaaagtc aataattccc aagtcttacg tctaagggga    13620
tataaggagg ttaaggatag aaaatcaggg cgatcaggag taggtctaac acttccatgt    13680
gataataggt atttatccca tcagataaga cttttcggga ttaatagtac tagctgcctg    13740
aaggctttgg agttaacata tttaatagga ccattgatag ataaaagtaa agatagatta    13800
ttcttaggag aaggtgcagg tgctatgttg tcatgttatg atgcaacgtt aggaccttca    13860
atgaactatt ataactcagg tgtttcatca tatgatataa atggtcagag ggaattaggg    13920
atctatccgt ctgaggctgc attagtggca agaaattga ataatgtaac taatttgggt    13980
caaagaatta aggtgctgtt caacggaaac cctgggtcta catgggttgg caaccaggaa    14040
tgcgaaacgt taatttggag tgaattacag gacaaatcaa tcggcttgat acattgtgac    14100
ctagaaggtg gagaactcaa agatacacaa acagtactgc atgaacatta tagtataatt    14160
aggatagcat atttagtagg ggataacgat gtcttattag tgactaaaat tgcacctaaa    14220
ttgggtacag attggactca gcaactatgc ttgtatctaa ggtattggaa tgaagtcaat    14280
ttagttgttc ttaagacatc taatccttct tctactgaga tgtatctgtt atcaaggaat    14340
ccaagtaaag atgtgattga ggatagtcta acagtaatct cagacctaaa gccattgtct    14400 aaaaagata gtatacaatt agaaaagtgg attttggttg agaaagacaa agttaaggaa    14460
tggctaatta agaattaag agaaggagaa ctaatgtcag gttcactcag gccttatcat    14520
caagcacttc agattttgg atttgaggcc aacttgcaca aattgtgtag agacttctta    14580
tcaactatga gtatttcaga tatccagatg tgtataaatt cattctacag agttttaaag    14640
gacacaatat ttgagtggag tcgggtaaca aatgatcaca agacatgtaa actcacaggg    14700
aaatatgagt tgtatcctat aagagacagt ggaaagttga agttatatc aagaggctt    14760 ataatatcct ggattgcttt atccatgtct actagactgt taacaggcac tttccctgat    14820
gttaagtttg agtccagatt gaatataggt ttagtctcct tatctacgaa tgagatcaaa    14880
tcacttaaac ttatatccaa ggctacggtg gataggtttc aagaagtgat tcacagtgta    14940
```

-continued

| | |
|---|---|
| tcctacagat tcttgactaa agaaattaaa atactcatga agatacttgg agctgttaaa | 15000 |
| ttatttggtg caagacagac ttataaccat ttagctttaa caccagaacc tctatctgat | 15060 |
| atagagggat atttagatga ttagctcgaa tatcaacagt aaacagctaa gaatcattaa | 15120 |
| gaagactatc tggatctaga cctaaatgaa agaataagaa aaacttattc aaacaatcaa | 15180 |
| agatctaagc aaaatgatat ctgc | 15204 |

```
<210> SEQ ID NO 2
<211> LENGTH: 15281
<212> TYPE: DNA
<213> ORGANISM: Porcine Parainfluenza Virus Type 1
<220> FEATURE:
<221> NAME/KEY: misc_feature
<222> LOCATION: (7989)..(7991)
<223> OTHER INFORMATION: n is a, c, g, or t

<400> SEQUENCE: 2
```

| | |
|---|---|
| ttgattttta agcatagtgc caccatggca gggttattaa gtgtctttga cacatttagt | 60 |
| tctaaaagga gtgagagcag atatagagga ggtggtggtg cggttatacc tggacaaaag | 120 |
| aacaccgtct cagtatttgt cctagggtca agtattgtag acgatagcga taagttagct | 180 |
| atagcactca tgttccttaac acatgctctt gatactgaca agcaacactc acaaagaagt | 240 |
| ggtttcctgg tttcattaat ggcaatggca tatagtagtc ctgaattata tctaacaact | 300 |
| aatggagtta atgcagatgt taagtatgtt atctacacaa ttgagcatga tccccagagg | 360 |
| acaacccata tgggttcat tgttaggaca agagatatgg actatgaaaa gacaacagag | 420 |
| tggctattca gccgtataac taataaatac ccattacttc agggacaaaa agacactcat | 480 |
| gatccagaat cactactcca gacttatgga tatccctcat gtttaggagc attgatagtc | 540 |
| caggtttgga ttgtcttggt caaagcaatt acaagtagtc tggattgaa gaaaggattc | 600 |
| ttcaataggc ttgaagcctt caggcaggat ggaacagtta aagctcatt agtcttcagt | 660 |
| ggagagacag ttgaggggat tgggtcagtg atgagatctc agcagagcct ggtgtcctta | 720 |
| atggtagaga ctctagttac catgaacacg gctagatctg acttgaccac tctagagaag | 780 |
| aatattcaga ttgttgggaa ttacatcaga gatgcgggtc ttgcttcatt catgaacacg | 840 |
| attagatatg gtgtggagac taagatggca gcacttacat tatctaatct tagacctgat | 900 |
| attaataaac taaagagttt aattgacatc tacttatcta agggtgcaag agccccccttc | 960 |
| atatgtatat tacgtgatcc agtacacgga gaatttgctc ctggaaatta tccagcattg | 1020 |
| tggagctatg ctatggggt cgcagtagtc cagaacaaag ctatgcagca gtatgtgaca | 1080 |
| gggaggacat atctggatat ggaaatgttc cttcttggtc aagcagtagc taaagatgca | 1140 |
| gaatctaaga tcagtaatgc attggaagat gaattaggta taactgaaaa tgccaaagac | 1200 |
| aggctcaaac atcatcttgc taacctttct ggaggtgatg agcttatca aaacccact | 1260 |
| ggtggaggag caatgaagt tataattgac aatgcagaca tagatctcag gacagaggaa | 1320 |
| accacagaag aatcttctat caggctttcc aatattgag aaaacaaagg gagaatagca | 1380 |
| gacgggcaga ggagatggga acaaccaga tccattggtg atgaccttaa tccagataac | 1440 |
| aacactgatg atgaagtatc cgctgcagaa aggaggattg cagaaagact ggcaaaaaag | 1500 |
| gaggggaaga atatcaagtc ggatatactc attactgatg gtatgactga agatacagat | 1560 |
| aacgatgatg atataatgag aatgaatgca ctaggaggaa tataaataat ccaaacaaag | 1620 |
| ggttttatat attggttaat aagaaaaact tagggtgaaa gaatagctcc tagatactag | 1680 |
| gaactctatc tctcccaaaa acaggatctc aaactggcca cccacaaaag aatccccaa | 1740 |

```
aatccagaga ccaaatggat caggatgccc tcttttctga agaatctatg gaggatcaga    1800
aggagggaca ctcaacaacc aacacactca ccagtgcagt tggactcatt gacatcatcc    1860
ttgccagtga gcccacagac attagaaaag atagaaaaca cctatgtgag cccatcacag    1920
cttggggaaa atcagaagca agcaagattt ctaagagtac agtctgtgaa gaaacccaa    1980 gaacagaaag ggaagatcat ggacaaagtg aaaagagtgg aattcttagg gagtcaaacg    2040
agtttgaagc agaagtttct cttagagaaa ctcatagccc agatacatca tggagggctt    2100
ggagaagaag tggtgcagac tctatacttg agaatatggg caatggatcc gactcctatg    2160
gcaacgaaat tactgaaat ggaggaagaa accagagaca agtcttgaa gctaaagttg    2220 gagagatgga tccgagttct aatacgagga gagaagacaa aactgaagga cttccagaag    2280
agatacgagg aggttcaccc atacctaatg acagagaagg tggaagaaat aataatggag    2340
gaagcctgga gtctgtcagc acacataatc caagagtaga aaataatatt atggatccaa    2400
ctcatcatct tgaagaagag gtacttaaga ggaacaagcc acgggagatg aatgctacaa    2460
gtcaatggtc gggtggatac aagactgatc aacaagacag taaacatgaa ttgataacta    2520
atccaatatt ttcaaatcaa aataggtcac agggcacaaa aaaggaaaaa gggaaagaat    2580
cagctgtaaa gcccaagacc agaaaatcca aatgtctcc tgaagacaca agaagcacag    2640
atcacatcta cgaagactct caagaacata caagaagaaa gaaaacagac aacgaatcat    2700
cacaaaagat tggtaaaaag ggcacagaag agaatacctt atatacagaa gaggtgatca    2760
aattgttagt gagtcttggt gtaatcccat ctgtagccgc attcaaccaa tcccgaaaca    2820
tatgccatgt atttgcaaaa cgtgtcctca attctgtgaa ctctgcagaa atgacagcta    2880
atatgtgcgg attattgcta tctgttgaga atcagtatc agaccagatt gaagaaaata    2940
agacactaat aaatcagatt ataagtgatt taagtacagg tagggaagtg cagaaacgtt    3000
tcactgagta tcaaaaggaa cagaattcat tgattatgtc aaatctggcg acacttcata    3060
tcataacaga tagaggagga aagaacaaca gcatggatac aggggagagg acaccatcaa    3120
tcaggaccaa ggggaaggag ccaacacaga gaacacaaag atttgatcca tctatggaat    3180
tcaccgagga gattaagtac aaacccgatc tatacaggga agacacattg agacaaagaa    3240
taacaaaccc tgtccttgat gagagtgcag agagaatcga caattcgaat gccgcgagac    3300
tgataccttg caaagaaaaa tcaacactgc gttcactcaa attgatcatt gagagcagca    3360
atttaagcag agcagacaaa attgcctata tcaggtcatt atcaaaatgc aaagatgaca    3420
aagaggtaga atcagtaatg aaactatttg aagaagatat agaatcaaat aatgaataat    3480
cactgatcag catatccaga aaacgtcaag acaagagtgt actgtgatga gtaatgactc    3540
tccaaatacc taataagaaa aacttagggt gcaagactca ccaaccaagc caagcaaatg    3600
gccgagatct acaagttccc caagctatca tatgaggaac atggatatat ggaacctcta    3660
ccactaaaga ctggcccaga taagaaggca gtcccacata taaggataat caagataggg    3720
gacccaccga agcatggaaa tcgatatctt gatattctct tacttgggtt ttatgagata    3780
cccaaagaag ttggaacata cggtagtgta tcagatttga cgagaccac gggatacaca    3840 atctgcggtt caggatcatt acctattgga attgctaggt acttaggtac agatcaggaa    3900
ctactcaaag catcagtaga gctaaaggtg acagtaagaa ggacagtaag gtcaagtgag    3960
atgattgtgt atatggtaga ttccatacca ccagcaatga tggcttgggc ttctaggctg    4020
aaacgaggca tgatattcaa tgcgaacaaa gtagcactag ctcctcaatg tctacctata    4080
```

```
gataaagata taagattcag agttgtctttt gtcaatggca cttctctagg ttccatcaca    4140
atagcaaaag ttcccaagac attagccgat cttgctttac cgaattccat atcggtcaat    4200
ttaatggtct cactcaagac tggtgcgtca actgagtcca agggcattat tcctacgcta    4260
aacgaaaagg gcgacaaggt actaaatttt atggtacacc tcggattaat acataggaaa    4320
gtcggaaggg tgtattcaat ggagtattgc aagggtaaaa tagagaagat gcggctgatc    4380
ttctcattag gactggttgg aggaatcagt ttccatgttc agcttacagg tgtggtatcc    4440
aaatcctttg ttggtcagct tggagggaga aaggaaatat gttacccttt gatggatgta    4500
aatccacaca tgaatttagt tatctgggct gcttccgttg aaatcactgg tgtggatgct    4560
gttttccaac cttccatacc aagagatttc aaatactacc caaatgtggt ggcaaaaaat    4620
attgggaaaa taaagcctta gagatccaaa gctactgcaa cctcagacat tcaatatta    4680
gactggtaag tgtcattata tgatcagcat cattcatcag aaataagaaa aacttagggt    4740
acaagttatc caaaaaagac agaacagaac aaacagatca agacaagaca tcacaaaatg    4800
cagaccatca tcctcagacc agccataata ctaagcatag cactactagt gaccagccaa    4860
gtccctagag ataaactagc aacttaggg atcatcgtta aggacagcaa agcactcaaa    4920
attgcaggat cttatgaaaa cagatacata gtcttaaacc ttgtaccaac aatagagaat    4980
gtgagtgggt gtggttccat ccaaatagca aaatataaag atgcttga aagattgtta    5040
ataccgataa aagatgcact agatttacaa gagtctttga tagtgattga taatgaaaca    5100
gtcaacaaca attatcgtcc tcagtataga tttgttggtg caattattgg gactatagcc    5160
cttggggtag caactgcggc ccaagttaca gcaggagtgg ctctgatgga ggcaagagag    5220
gccaaaagag atatatcagt gttaaaagaa gcaattggaa agactcaaaa ctcaattgaa    5280
aaattacaga attctgcagg tgaacagata ctggctctca aaatgctcca ggattatgtc    5340
aatggagaga tcaaaccagc tattgaagaa cttggatgtg agactgctgc acttaaatta    5400
ggaattgcac ttacacaaca ctacacagag ctcacaaatg cctttgggtc gaatctaggt    5460
tccataggag agaagagctt aacattacag gccctatcat cattatacaa gaccaatata    5520
actgatatac tgcaacaac taatctcggg aaaacagata tttatgatat tatatatgct    5580
gagcaggtta aggaagagt aatagatgtc gatcttagac gatatatggt tacaatatct    5640
gtaaagttac caatattatc agaaatacca ggagtattga tctatgaagt ctcctctata    5700
tcttacaata tagatggaac agagtggtat gccgctgtac ctgaccacat attaagtaaa    5760
tccgcatata tcgggggtgc agatataagc gattgtatag atctggatt gacatatatt    5820
tgtccgcgag atcctgctca aattatagca gataaccaac agcaatgttt tttaggtcat    5880
cttgacaagt gccctataac taagtagtt gataatcttg tgcctaaatt tgcattcata    5940
aatggtggag tagttgcaaa ctgtatagcc tctacatgta cctgtggaga aagagggtc    6000
caggtctctc aagatagaaa taaggagta accttttttga ctcataataa ttgtggatta    6060
atagggataa acgggatgga atttcatgct aacaagaaag ggagtgatgc tacttggaat    6120
gtctccccca taggagtagg gccagcagta tcgttaagac ctgtagatat atctttacaa    6180
atagtttctg ctactaattt tctaaactca tcacgaaaag atcttatgaa ggcaaaagag    6240
atcttaaacc aggtaggata tcttagagat ttaaccgtca taacaataat taatatagta    6300
attatagcta tattacttat atgtgtaact ggattaggcg tactgtatca ccaattgaga    6360
agtgcactag tgatgagaga caagatgtca gtactaaata atagttctta ttctttagaa    6420
ccaagaaccg cccaggtaca agtaattaag cctactagtt tcatgggata aactataaaa    6480
```

```
atatatttta atccatcctc attaatcaaa gtaaagaaaa cttagggtgc acgacagtaa    6540
ctcaccacca aaggagaaat agatcagaga ccaacacatc aagagatgga aggggccaaa    6600
gttaagacat cagagtactg ggccaagagt cctcaaattc acgtaacaaa taatcctaac    6660
gtacaaaaca gagagaagat caaggaaaca ttaataattt taatatcatt catttctttc    6720
ttatctcttg tactggttat agctgtactg ataatgcaat ctttacataa cggcacaata    6780
ctaaggtgta aagatgtagg cctagaatct atcaataaat ccacttactc tatatctaat    6840
acaattctgg acgtcatcaa acaagagctg ataactcgta taataaatac tcaaagttct    6900
gtgcaggtag ctctcccagt cttaattaac aagaaaatcc aggatctctc actaaccatt    6960
gagaaaagtt caaaagtgca tcaaaattct cctacttgta gtggtgtggc tgctctgaca    7020
catgtagaag ggataaaacc cttggatcca gacgattact ggaggtgtcc aagtggggaa    7080
ccatatctag aggatgaatt gacattaagc cttatccctg acctagtat gctggctgga     7140 acctctacca ttgatggctg tgtaagatta ccatcccttg caataggaaa atcgctatat    7200
gcctatagtt ccaaccttat aactaagggt tgtcaagaca tagggaaatc ctatcaagtg    7260
ctacagttag gtattataac tctgaattca gacttacatc ctgatttaaa tcctataata    7320
tcacatactt atgatataaa tgataataga aagtcctgtt ctgttgctgt atcagaaact    7380
aaaggatacc aattatgctc gatgccgcgt gtcaacgaaa aaacagatta cactagtgat    7440
ggtattgaag atatagtctt tgatatactt gatctcaaag ggtcctctag aagtttcaaa    7500
ttttcaaaca atgatataaa ctttgatcat cctttctcag cgttataccc tagtgtagga    7560
agtggtatta tatggaaaaa tgaactgtat ttcttaggtt atggggctct gacaactgca    7620
cttcaaggga atacaaaatg taatttaaag ggatgtccag gagcaacaca aaacaactgc    7680
aacaagttca tctctagttc atggttatac agcaaacaga tggttaatgt actgatacag    7740
gttaaggggt atttatctaa caagccaagt attatagtta gaacaatccc aataacagaa    7800
aattatgtag gagcagaagg gaaactagta ggaacacgtg agagaatata tatatataca    7860
agatcaacgg gttggcatgc caatttacaa ataggagtac ttaatataaa tcatccaata    7920
accataactt ggacagatca caaagtacta tcaagaccag gaagaagtcc ttgtgcctgg    7980
aataacaann ncccctagaaa ttgtactact ggtgtataca cagatgctta tcctatatcg    8040
cctgatgcca attatgttgc tacagttact ttattatcta attcaacacg aactaatcct    8100
actattatgt attcatcttc tgatagagta tataacatgt taagattaag aaatactgaa    8160
ttagaagctg catacacaac cacgtcttgt attgtccact ttgatagagg ttattgtttt    8220
catattatag aaattaatca aaaagaactg aatacactac agcctatgct ctttaagact    8280
gcaattccta aagcttgcag gataagcaat ttataagaca cctattgaaa taataatctg    8340
tatctaatta cttaaaaggg tgactgtgca tgacttagag ataagtgacc tgtggacata    8400
aatcatacag gtcattaact agcatataat acatctaata agaaaaactt aggttgaatg    8460
ccaaagcatt caaccagaat ggatcatttc aatatgtctc aaaatccaaa tgatatacta    8520
taccctgaat gccacttgaa ctctccagtt gtgaaaggga agatcgctca gctacatgtc    8580
ttgttggata ttaatcagcc atatgaaatg agggaccta gtataataga aatcacgaaa    8640
gttaaaatta aatctggagg gttaaatcaa aggttaatca gaatcagatc tttagggaaa    8700
gagatgagga gaatcatatc tgattttgat aagtatacat tcgaacctta cccaatattt    8760
tctaaagaat tatttagatt agagatacca gagatttgtg ataaaattca atcagttttt    8820
```

```
gcagtgtcgg ataagttaag caaagatata tcccaaccat tacaatactt atggagagat    8880
gtgcgtaggc agttgggagg ggattgttcc aaggatcttt ctaacaatga gattgatata    8940
cacaaaattc ctgaaatcca tactaaattc accagaaata actggtataa accattcatg    9000
acatggttta gtatcaaata tgatatgaga agatgtcaaa agaatagggaa aaacataaac    9060 ttagacagta ggcaatcata taattatctt aactgtaaat actattttat aattatccac    9120
ccggatctct taatgatatt ggacaagatc aaatacacgg gatacttact gacaccagaa    9180
ttagtgctaa tgtactgtga tgtggtcgaa ggtagatgga acatgtctgc cgctggacaa    9240
ttagatgaca aatcacacaa aataacatta aaaggagaag aattgtggag caggatagat    9300
gaattattca agataatcgg ggaagagaca tttaacatca tatcactatt ggagccatta    9360
tctttagcat tgatacaatt aacagatcct gttatgtctt taaaaggtgc atttatgaga    9420
catgtcatct cagaaatgaa tgaaatattg gtaaatgtg gaaatctaac tgaacttgag    9480
gtggatcaca taatggattc aatccttaac attttttatgg atacaacagt agatgagaaa    9540
gcagagatct tctccttctt taggacattt ggtcatccta gccttgaggc ctccatagct    9600
gctgaaaaag ttaggcaaca tatgtatgcg cagaaaagta taaatataa gaccttatgt    9660 gagtgtcacg ctatattttg tacaattata ataaacggat atagagacag gcacggagga    9720
caatggcccc cctgtcagtt cccagatcat gtgtgtcaag aactcagaaa ttctcaagga    9780
tctaattcag ctatatctta tgaaacagcc gttgataatt tcgagagttt tataggtttt    9840
agattcgaga agttcataga ccctcaatta gatgaagatc tcactattta tatgagagat    9900
aaagcattgt ctccaagaag agaagcctgg gattctgtgt atccagatgg caatctgctg    9960
tataaagtgc cgttctccga agaaacaagg agattgatag aagtctttat cagtgattct   10020
aattttaatc cagaagacat tatacaatat gtagagacag gagaatggtt gaacgatgat   10080
actttcaaca tatcttatag cctaaaagaa aaggagatca acaagagggt cgattgttt   10140 gccaagatga catacaaaat gagagcagtc caagtattgg cagaaacttt gctagcaaaa   10200
ggaataggag gttttgttta atgaaaatggt atggttaaag gtgaaatcga tttactaaag   10260
agtctaacta ctttatctat atcaggagtt ccaaggacta acgagattta taatgaatca   10320
gttagtgaag aagctgatag gagaagatgg gaaagagaaa attcctcata ctattgggat   10380
aaaaggaaaa aatcaaaaca tgagttcaaa gccacagact catctactaa cggctatgaa   10440
actctaagct gttttcttac tacggacttg aagaaatatt gtctaaattg gagatttgag   10500 agtcacatctc tattcgggca gagatgtaac gaaatatttg ggttcaagag attcttcaac   10560
tggatgcatc ctgtattgga agaatgtaca atatatgtgg gtgatcctta ctgtcccgtg   10620
cctgataaaa tccacaagaa tttagaagat catgaagatt caggcatctt tatacataga   10680
ccgaagggtg ggatagaagg ttattgtcaa aaactttgga ctctcatatc cataagcgca   10740
attcatctag ctgctgtcaa ggtcggggtt agagtatcag ctatggtaca aggtgacaac   10800
caagcaattg ccgtgacatc tagggtacca gtgacggcca cgtacaagtt caaaaaagag   10860
caggtatata cggagatcac taagtatttt aagtctttaa gagatgtgat gtctaattta   10920
ggacatgaac tcaaactcaa cgagacaatt ataagtagca agatgttcgt gtatagtaag   10980
cggatatatt atgatggtaa aatactaccc caatgtttaa aagcacttac aaggtgtgtt   11040
ttttggtccg agaccttggt ggatgaaaac aggtctgcgt gctctaatct tgcaactgct   11100
atagccaaag ctatagaaaa tggctattca ccaatattag ttactcaat agctctgtat   11160 aagacttgtc agcaagtatg tatttcatta gggatgacta tcaatcctac aataacacct   11220
```

```
aatataagag accaatatta tttagggaag aattggctta gatgtgcagt tttgatacct    11280
gctaatgtag ggggatttaa ctacatggca atgtctagat gcttcgtcag aaatataggc    11340
gaccctgcag tagctgctct agcagacctc aaaaggttta tccgagcagg actattggac    11400
aagcagattt tgtaccgtgt aatgaatcag gaatctgggg agtctaattt cttagactgg    11460
gcatctgatc catactcatg taatttaccg cattcgcaga gtatcacaac aattataaag    11520
aatattacag ctcgttcagt tctccaagag tcaccaaatc ccttactttc aggtttattt    11580
acatgtgaca gtaaagaaga agacttaaat ttagcgacat ttctgatgga caggaaggtc    11640
atattgccaa gagttgcaca tgagatacta gataactctt tgacagggat cagagaatct    11700
atcgcaggaa tgctggacac tacaaaatca ttagtacggg ttagtattag aaaggggggt    11760
ttatcataca atctcttaag gaagctgata aattatgatt tattacaata tgaaacatta    11820
accaggactt taaggaaagt cgtcacaaat aacattgaat atgaatatat gtgttctgta    11880
gaattagcaa ttggattaag gcaaaaaatg tggtcacatc taacatatgg gagacctata    11940
catggattag aaacacctga tcctctagaa ctccttaaag gaacattcat caaaggatct    12000
gaggtttgca agtatgcag gtctgaaggt gataatccta tatatacttg gttttattta    12060
cctgaggaaa tagatctgga taacctagaa caaggaaatc catctataag aataccttac    12120
tttgggtcta ctactgacga aagatcagaa gcacaactgg gttatgttaa aacactaagt    12180
aaacctgcta agcagcgat taggattgct atgatatata cttgggctta tggtactgat    12240
gagatatcat ggatggaagc ggctcaaatt gcacaaacaa gagcaaattt aagtcttgat    12300
aatttgaaac ttctgactcc ggtatcaaca tctacaaatc tgtcccatag attaaaggac    12360
actgctaccc agatgaaatt ctcaagtgca actctagtta gagctagtag atttattact    12420
atatcaaatg ataagatggc tctgaaggag gcaggtggga caaaggatac taatttaata    12480
tatcagcaga taatgttgac aggacttagt gtttttgaat tcaataccag atacattaaa    12540
ggtaagacta aacaaccaat gatcctacac ttacatttaa acaatggctg ctgcataatg    12600
gaatcaccac aagagacttg tatccctcct aaatctactc tagacttaga ggtatataat    12660
gaagaaaata aattaatata tgataataat ccattaaaaa atgttgatct cggtatttc    12720 caaaaaatta gagatatcgt gcacactgtg gatatgactt tctggtctga tttggaaata    12780
atgagagcag ttactatttg tacatctatg acaaatagcag ataccatgtc tcaattggat    12840
agagataacc ttaaagaagt aattgttctt acgaatgatg atgacattaa tagcttaata    12900
acagagttta tgataataga tatcccactc ttttgctcaa cattcggagg aatcttagta    12960
aatcagtttg cctatgcatt atacggtcta aatataagag gtagagaaga aatatggggt    13020
tacattacac ggactttaaa agatacttct catgctgtgt taaaggtact tgctaatgca    13080
ttatcacatc caaggtgtt caagagattc tgggattcg gtattttaga gcctgtatat    13140
ggacctaatt tatccaacca agataagata atgttagcat tatctgtttg tgagtactca    13200
atagacttat tcatgagggact ctggcaaagc ggaatacctc tagaaacctt tatatgtgac    13260
aatgatccag aagtagttga attaagaaaa ggtgcctact ggcaagaca tttagcatat    13320 ttatgcagct taggagagat ttcctcatat ggtcctagat tagaaactct aacatcatta    13380
gaaaggttag aagttcttaa aagctaccta gagatatctt gtttagagga tccaacattg    13440
agatacagtc aggttacagg gctggtatta aaagtgttcc catcaacagt agtatatatc    13500
aggaagttag ctataaaaat gttgaggatt aggggcatag gggtgccaga ggtgttagaa    13560
```

-continued

```
gactgggatc ccagtcatga caagctcta ctagataata tagctcaaga gatccaacat    13620
aatatcccaa taaaccaatc tatcaagaca cctttctggg ggctcaaagt caataattcc    13680
caagtcttac gtctaagggg atataaggag gttaaggata gaaaatcagg gcgatcagga    13740
gtaggtctaa cacttccatg tgataatagg tacttatctc atcagataag acttttcggg    13800
attaatagta ctagctgcct gaaagctttg gagttaacat atttaatagg accattgata    13860
gataaaagta agatagact attcttaggg gaaggtgcag gtgctatgtt atcatgttat    13920
gatgcaacgt taggacctttc aatgaactat tataactcag gtgtctcatc atatgatata    13980
aatggtcaga gggaattagg aatctatcca tctgaggctg cattagtggc aaagaaattg    14040
aataatgtaa ctaatttggg tcagagaatt aaggtgctgt tcaacggaaa ccctgggtct    14100 acatggttg gcaaccagga atgcgaaaca ttaatttgga gtgaattaca ggacaaatca    14160
atcggcttga tacattgtga cctagaaggt ggagaactta agatacaca aacagtactg    14220 catgaacatt atagcataat taggatagca tatttagtgg gagataacga tgttttatta    14280
gtgactaaaa ttgcacctaa attgggtaca gattggactc agcaactatg cttgtatcta    14340
aggtattgga atgaagtcaa tttagttgtt cttaagacat ctaatccttc ttctactgag    14400
atgtatttgt tatcaaggaa tccaagtaaa gatgtgattg aggatagtct aacagtaatc    14460
tcagacctaa agccattgtc taaaaaagat agtatacaat tagaaaagtg gattttggtt    14520
gagaaagaca aagttaagga atggctaatt aaagaattaa gagagggaga actaatgtca    14580
ggttcactca ggccttatca ccaagcactt cagatttttg gatttgaggc caacttgcac    14640
aaattgtgta gagacttctt atcaactatg agtatttcag atatccagat gtgtataaat    14700
tcattctaca gagttttaaa ggacacaata tttgagtgga gtcgggtaac aaatgatcac    14760
aagacatgta aactcacagg gaaatatgag ttgtatccta aagagacag tggaaagttg    14820 aaagtgatat caagaagact tataatatcc tggattgctt tatccatgtc tactagactg    14880
ttaacaggcg ctttccctga tgttaagttt gagtccagat tgaatatagg tttagtctcc    14940
ttatctacga atgagatcaa atcacttaaa cttatatcca aggctacggt ggataggttt    15000
caagaagtga ttcacagtgt atcctacaga ttcttgacta agaaaattaa aatactcatg    15060
aagatacttg gagctgttaa attatttggt gcaaggcaga cttataacca tttggcttta    15120
acaccagaac ctctatctga tatagaggga tattttgatg attagctcaa atatcaacag    15180
taaacagcta agaatcatta agaagactat ctggatccag acctaaatga aagaataaga    15240
aaaacttatt caaacaatca aagatctaag caaaatgata t                       15281
```

<210> SEQ ID NO 3
<211> LENGTH: 24
<212> TYPE: DNA
<213> ORGANISM: Porcine Parainfluenza Virus Type 1

<400> SEQUENCE: 3

```
agcagaggag atgggaaaca acca                                          24
```

<210> SEQ ID NO 4
<211> LENGTH: 22
<212> TYPE: DNA
<213> ORGANISM: Porcine Parainfluenza Virus Type 1

<400> SEQUENCE: 4

```
cggatacttc atcgtcagtg tt                                            22
```

-continued

```
<210> SEQ ID NO 5
<211> LENGTH: 23
<212> TYPE: DNA
<213> ORGANISM: Porcine Parainfluenza Virus Type 1

<400> SEQUENCE: 5
tggagacaac aaagggagaa tag                                         23

<210> SEQ ID NO 6
<211> LENGTH: 20
<212> TYPE: DNA
<213> ORGANISM: Porcine Parainfluenza Virus Type 1

<400> SEQUENCE: 6
ttagggtgca cgacagtaac                                             20

<210> SEQ ID NO 7
<211> LENGTH: 18
<212> TYPE: DNA
<213> ORGANISM: Porcine Parainfluenza Virus Type 1

<400> SEQUENCE: 7
gtccacaggt cacttatc                                               18

<210> SEQ ID NO 8
<211> LENGTH: 22
<212> TYPE: DNA
<213> ORGANISM: Porcine Parainfluenza Virus Type 1

<400> SEQUENCE: 8
ttagggtgca cgacagtaac tc                                          22

<210> SEQ ID NO 9
<211> LENGTH: 22
<212> TYPE: DNA
<213> ORGANISM: Porcine Parainfluenza Virus Type 1

<400> SEQUENCE: 9
ccacagatca cctgtctcta ag                                          22

<210> SEQ ID NO 10
<211> LENGTH: 16
<212> TYPE: DNA
<213> ORGANISM: Porcine Parainfluenza Virus Type 1

<400> SEQUENCE: 10
cggtgagaaa ggatga                                                 16

<210> SEQ ID NO 11
<211> LENGTH: 18
<212> TYPE: DNA
<213> ORGANISM: Porcine Parainfluenza Virus Type 1

<400> SEQUENCE: 11
caaagggtcc tctagaag                                               18
```